(12) United States Patent
Prakash et al.

(10) Patent No.: US 10,039,834 B2
(45) Date of Patent: Aug. 7, 2018

(54) COMPOSITIONS AND METHODS USING REBAUDIOSIDE X TO PROVIDE SWEETNESS ENHANCEMENT

(71) Applicants: Indra Prakash, Alpharetta, GA (US); Juvenal Higiro, Manhattan, KS (US); Mary Campbell, Acworth, GA (US)

(72) Inventors: Indra Prakash, Alpharetta, GA (US); Juvenal Higiro, Manhattan, KS (US); Mary Campbell, Acworth, GA (US)

(73) Assignee: The Coca-Cola Company, Atlanta, GA (US)

( * ) Notice: Subject to any disclaimer, the term of this patent is extended or adjusted under 35 U.S.C. 154(b) by 0 days.

(21) Appl. No.: 14/036,654

(22) Filed: Sep. 25, 2013

(65) Prior Publication Data
US 2015/0018432 A1    Jan. 15, 2015

Related U.S. Application Data

(60) Provisional application No. 61/845,812, filed on Jul. 12, 2013.

(51) Int. Cl.
*A61K 47/36* (2006.01)
*A23L 2/60* (2006.01)
*A23L 27/30* (2016.01)

(52) U.S. Cl.
CPC .......... *A61K 47/36* (2013.01); *A23L 2/60* (2013.01); *A23L 27/36* (2016.08)

(58) Field of Classification Search
None
See application file for complete search history.

(56) References Cited

U.S. PATENT DOCUMENTS

| 7,160,565 | B2 * | 1/2007 | Rifkin ..................... 426/72 |
| 2008/0102162 | A1 | 5/2008 | Delcour et al. |
| 2009/0004360 | A1 | 1/2009 | Bingley et al. |
| 2010/0092638 | A1 † | 4/2010 | Hansen |
| 2011/0160311 | A1 † | 6/2011 | Prakash |
| 2011/0183056 | A1 * | 7/2011 | Morita et al. .............. 426/442 |
| 2013/0064955 | A1 | 3/2013 | Miguel et al. |
| 2013/0136839 | A1 | 5/2013 | Putter et al. |

FOREIGN PATENT DOCUMENTS

| WO | WO 2010038911 A1 | 4/2010 |
| WO | WO 2011/028671 A1 * | 3/2011 |
| WO | WO 2013/022989 | 2/2013 |
| WO | WO 2013/092657 | 6/2013 |
| WO | WO 2013096420 A1 | 6/2013 |

OTHER PUBLICATIONS

International Search Report for PCT/US2014/046499, dated Oct. 16, 2014.
Masaya Ohta: "Characterization of Novel Steviol Glycosides from Leaves of Stevia rebaudiana Morita", J. Appl. Glycosci., vol. 57, Aug. 17, 2010 (Aug. 17, 2010), pp. 199-209.
Supplementary European Search Report for European Patent Application No. 14822472.8, dated Dec. 16, 2016.

* cited by examiner
† cited by third party

*Primary Examiner* — Terry A McKelvey
*Assistant Examiner* — Catheryne Chen
(74) *Attorney, Agent, or Firm* — King & Spalding

(57) ABSTRACT

Sweetened compositions comprising at least one sweetener and rebaudioside X are provided herein. Rebaudioside X is present in the sweetened compositions in a concentration at or below the sweetness recognition threshold, while the at least one sweetener is present in a concentration above its sweetness recognition threshold. Rebaudioside X acts to enhance the sweetness of the sweetened compositions, e.g. beverages and concentrate compositions, thereby allowing for preparation of sweetened compositions with reduced calorie content. Methods of enhancing the sweetness of a sweetened composition with rebaudioside X are also provided herein.

7 Claims, 4 Drawing Sheets

COMPOSITIONS AND METHODS USING REBAUDIOSIDE X TO PROVIDE SWEETNESS ENHANCEMENT

CROSS REFERENCE TO RELATED APPLICATIONS

This application claims priority under 35 U.S.C. § 119 to U.S. Provisional Patent Application No. 61/845,812, filed Jul. 12, 2013. The contents of the above-referenced priority document is hereby fully incorporated herein by reference.

FIELD OF THE INVENTION

The present invention relates generally to the use of rebaudioside X as a sweetness enhancer. The present invention provides sweetened compositions (e.g., beverages) and concentrate compositions comprising at least one sweetener and rebaudioside X. The present invention also relates to methods for enhancing the sweetness of a sweetened composition using rebaudioside X.

BACKGROUND OF THE INVENTION

Natural caloric sugars, such as sucrose, fructose and glucose, are utilized to provide a pleasant taste to beverages, foods, pharmaceuticals, oral hygienic and cosmetic products. Sucrose, in particular, imparts a taste preferred by consumers. Although sucrose provides superior sweetness characteristics, it is caloric. Non-caloric or low caloric sweeteners have been introduced to satisfy consumer demand. However, sweeteners within this class differ from natural caloric sugars in ways that consumers do not perceive the same taste quality. On a taste basis, non-caloric or low caloric sweeteners exhibit a temporal profile, maximal response, flavor profile, mouth feel, and/or adaptation behavior that differ from sugar. Specifically, non-caloric or low caloric sweeteners exhibit delayed sweetness onset, lingering sweet aftertaste, bitter taste, metallic taste, astringent taste, cooling taste and/or licorice-like taste. On a source basis, many non-caloric or low caloric sweeteners are synthetic chemicals. The desire for a natural non-caloric or low caloric sweetener that tastes like sucrose remains high.

*Stevia rebaudiana* Bertoni is a perennial shrub of the Asteraceae (Compositae) family native to certain regions of South America. Its leaves have been traditionally used for hundreds of years in Paraguay and Brazil to sweeten local teas and medicines. The plant is commercially cultivated in Japan, Singapore, Taiwan, Malaysia, South Korea, China, Israel, India, Brazil, Australia and Paraguay.

The leaves of the plant contain a mixture containing diterpene glycosides in an amount ranging from about 10 to 20% of the total dry weight. These diterpene glycosides are about 150 to 450 times sweeter than sugar. Structurally, the diterpene glycosides are characterized by a single base, steviol, and differ by the presence of carbohydrate residues at positions C13 and C19. Typically, on a dry weight basis, the four major steviol glycosides found in the leaves of *Stevia* are Dulcoside A (0.3%), Rebaudioside C (0.6-1.0%), Rebaudioside A (3.8%) and Stevioside (9.1%). Other glycosides identified in *Stevia* extract include Rebaudioside B, D, E, and F, Steviolbioside and Rubusoside. Among these, only Stevioside and Rebaudioside A are available on a commercial scale.

The use of steviol glycosides has been limited to date by certain undesirable taste properties, including licorice taste, bitterness, astringency, sweet aftertaste, bitter aftertaste, licorice aftertaste, and become more prominent with increase of concentration. These undesirable taste attributes are particularly prominent in carbonated beverages, where full replacement of sugar requires concentrations of steviol glycosides that exceed 500 mg/L. Use of steviol glycosides at such concentrations results in significant deterioration in the final product taste.

Accordingly, there remains a need to address the taste issues of natural sweeteners and reduce caloric content of compositions containing traditional sweeteners.

SUMMARY OF THE INVENTION

In one embodiment, the present invention provides a sweetened composition comprising at least one sweetener and rebaudioside X, wherein the at least one sweetener is present in a concentration above its sweetness recognition threshold, wherein rebaudioside X is present in a concentration at or below its sweetness recognition threshold, and wherein rebaudioside X enhances the sweetness of the sweetened composition by an amount more than the detectable sweetness of a solution containing the same concentration of rebaudioside X in the absence of the at least one sweetener and/or the rebaudioside X enhances the sweetness of the sweetened composition by about 1.0% (w/v) sucrose equivalence or greater, such as, for example, about 1.5% (w/v) or greater. In another embodiment, the rebaudioside X enhances the sweetness of the sweetened composition from about 1.0% to about 3.0% (w/v) sucrose equivalence.

The present invention also provides a method for enhancing the sweetness of a sweetened composition comprising at least one sweetener in a concentration above its sweetness recognition threshold, said method comprising adding rebaudioside X to the sweetened composition in a concentration at or below its sweetness recognition threshold, wherein the rebaudioside X enhances the sweetness of the sweetened composition by an amount more than the detectable sweetness of a solution containing the same concentration of rebaudioside X and/or the rebaudioside X enhances the sweetness of the sweetened composition by about 1.0% (w/v) sucrose equivalence or greater.

In preferred embodiments, the rebaudioside X has a purity from about 80% to about 99%, i.e. rebaudioside X accounts for about 80% to about 99% by weight of the *Stevia* extract or mixture of steviol glycosides. In a preferred embodiment, the rebaudioside X has a purity greater than about 95%.

The sweetener can be any natural or synthetic sweetener. In a preferred embodiment, the sweetener is a caloric sweetener. In another embodiment, the sweetener is a carbohydrate sweeteners such as, for example, sucrose, fructose, glucose, high fructose corn syrup, high fructose starch syrup and/or combinations thereof. In still another embodiment, the sweetener is a rare sugar, such as, for example, D-psicose, D-allose, D-turanose, D-tagatose, D-trehalose, D-leucrose, rare sugar syrup and/or combinations thereof.

The sweetened composition is selected from the group consisting of pharmaceutical compositions, edible gel mixes and compositions, dental compositions, foodstuffs, confections, condiments, chewing gum, cereal compositions, baked goods, dairy products, tabletop sweetener compositions, beverages and beverage products.

The sweetened compositions of the present invention may further comprise any number of functional ingredients and/or additives.

In a preferred embodiment, the sweetened composition is a beverage. The beverages comprise a liquid matrix. In some embodiments, the beverage is a reduced-calorie beverage.

In another embodiment, the present invention also provides a concentrate composition comprising at least one sweetener and rebaudioside X, wherein the at least one sweetener is present in the beverage in a concentration above its sweetness recognition threshold and the rebaudioside X is present in a concentration at or below it sweetness recognition threshold once the concentrate composition is either (i) added to the full-strength beverage or (ii) diluted to a full-strength beverage, and wherein the concentrate composition enhances the sweetness of a beverage by an amount more than the detectable sweetness of a solution containing the same concentration of rebaudioside X in the concentrate composition and/or the concentrate composition enhances the sweetness of the beverage containing at least one sweetener by about 1.0% (w/v) sucrose equivalence or greater.

Suitable concentrate compositions include, for example, syrups, powdered beverages, flavor packets or flavor enhancer drops.

DETAILED DESCRIPTION OF THE INVENTION

Figure 1:
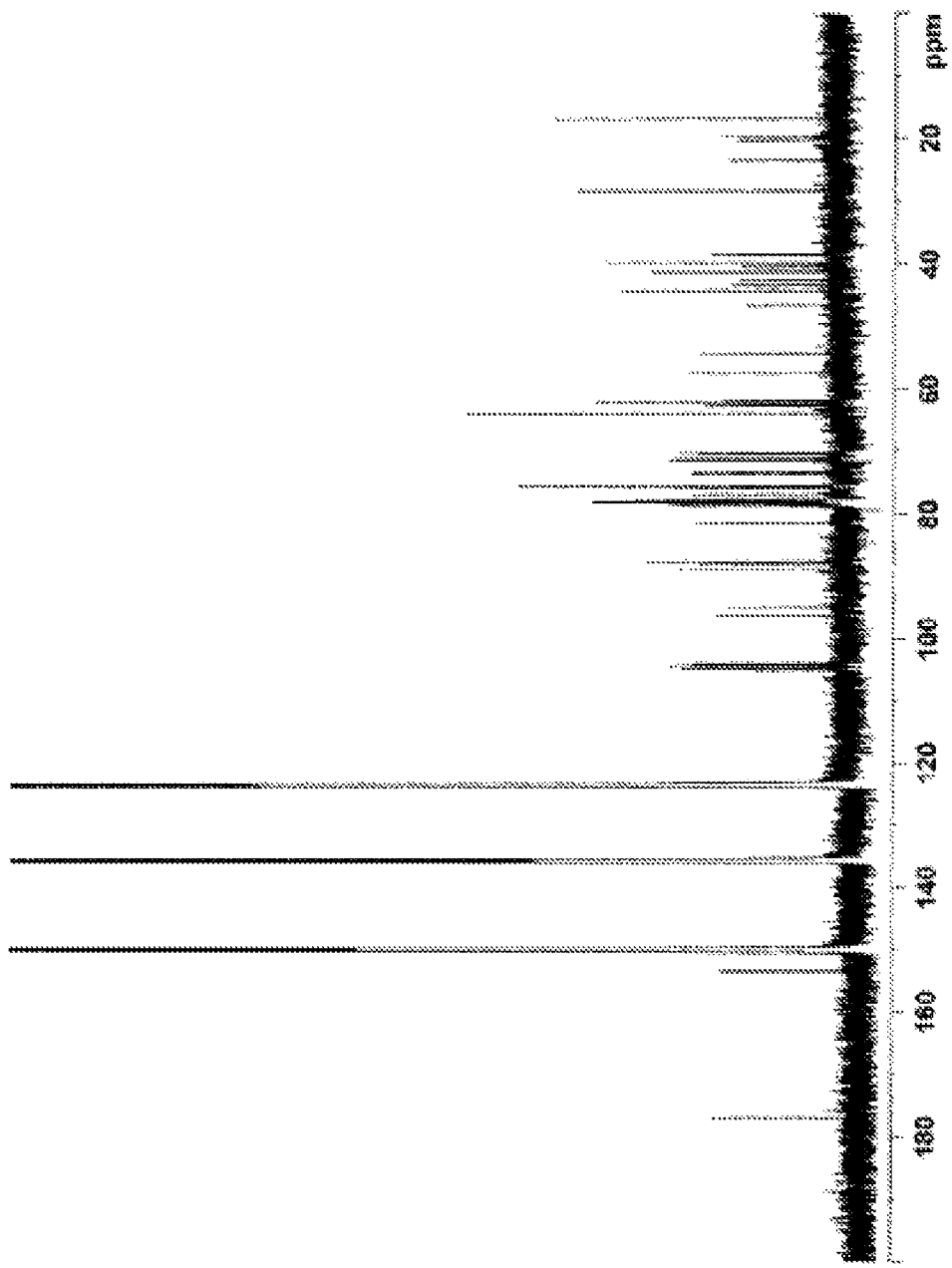
FIG. 1: illustrates the $^{13}$C NMR spectrum of Reb X (150 MHz, $C_5D_5N$).
Figure 2:
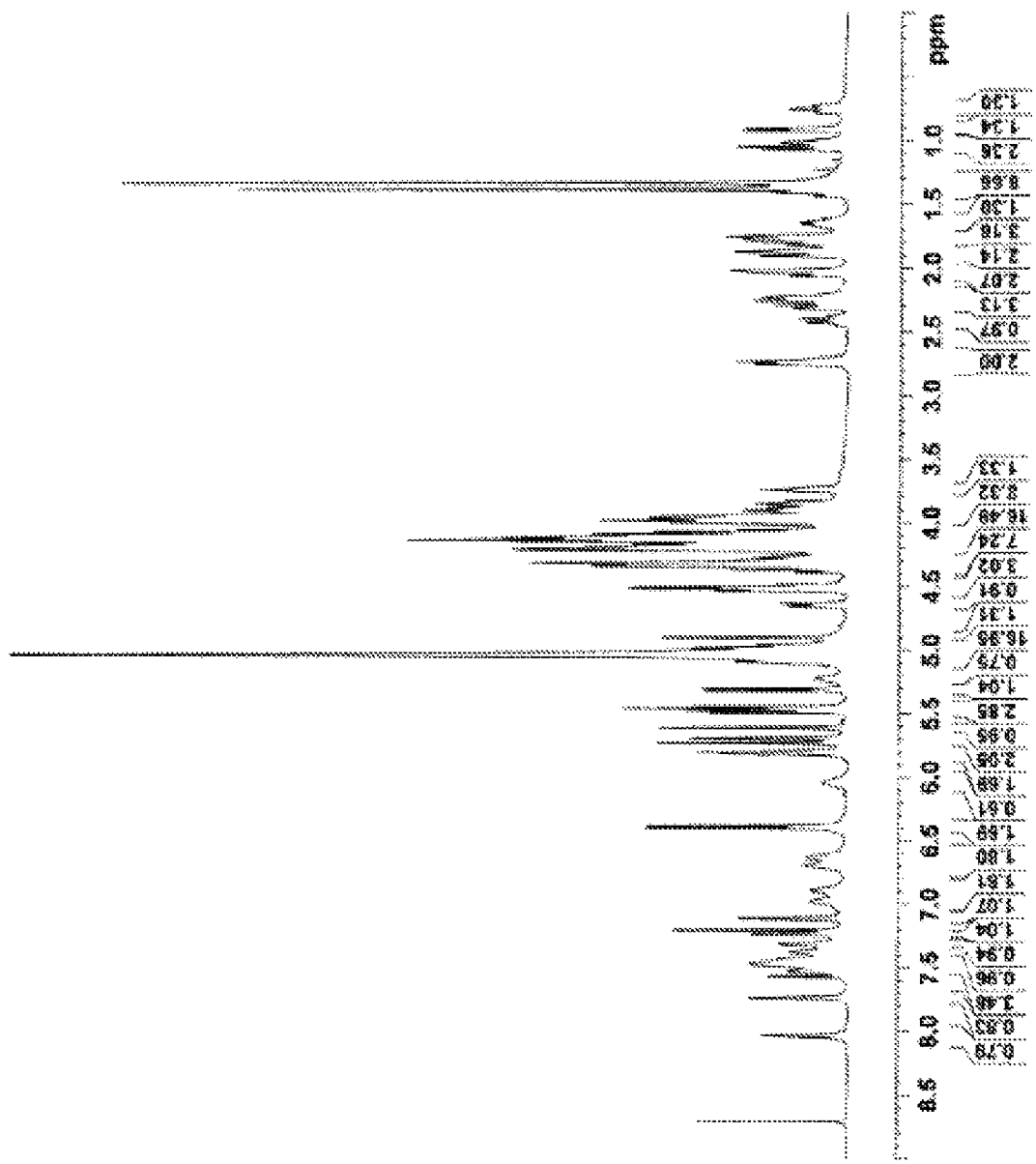
FIG. 2: illustrates the $^1$H NMR spectrum of Reb X (600 MHz, $C_5D_5N$).
Figure 3:
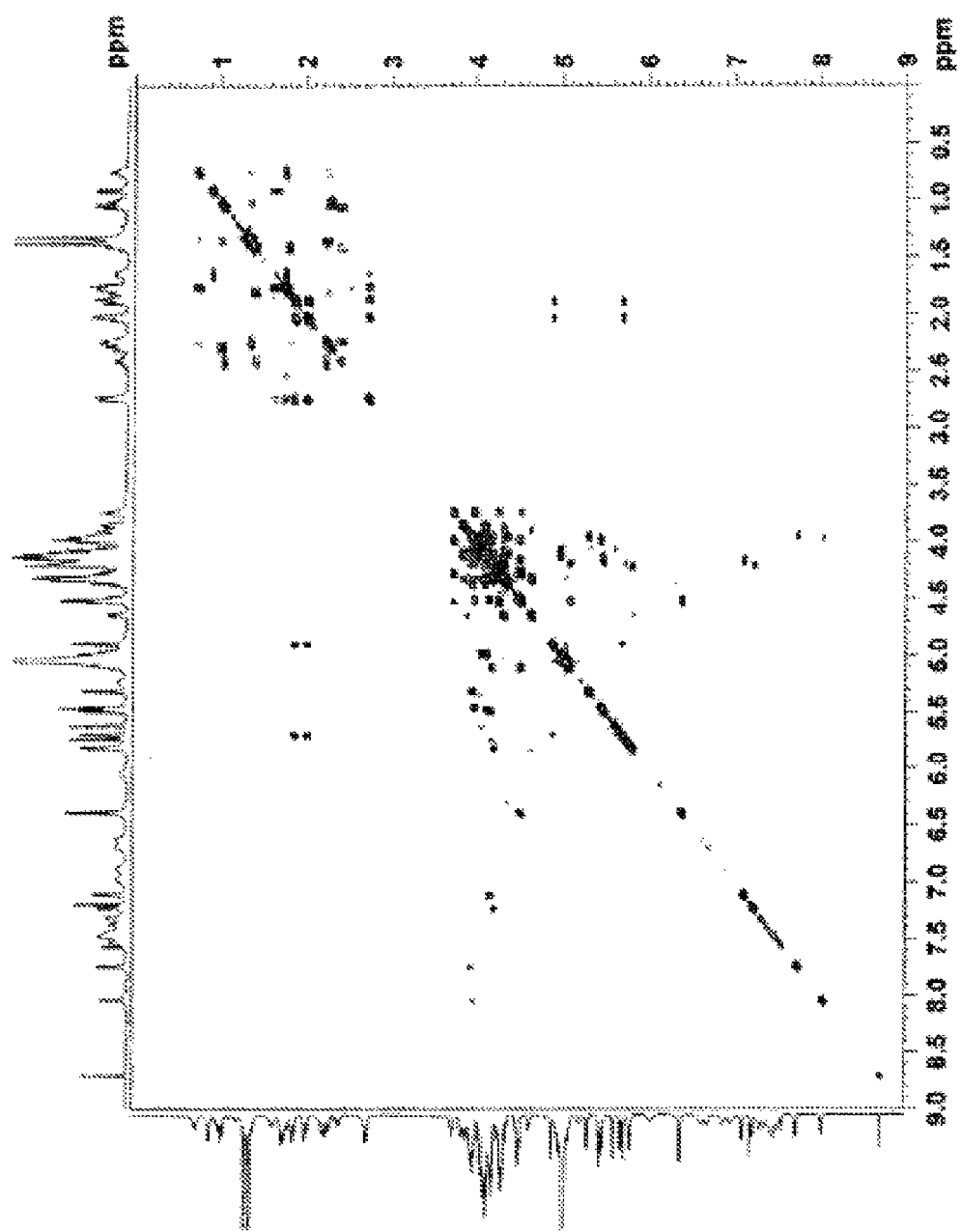
FIG. 3: illustrates the $^1$H-$^1$H COSY spectrum of Reb X (600 MHz, $C_5D_5N$).
Figure 4:
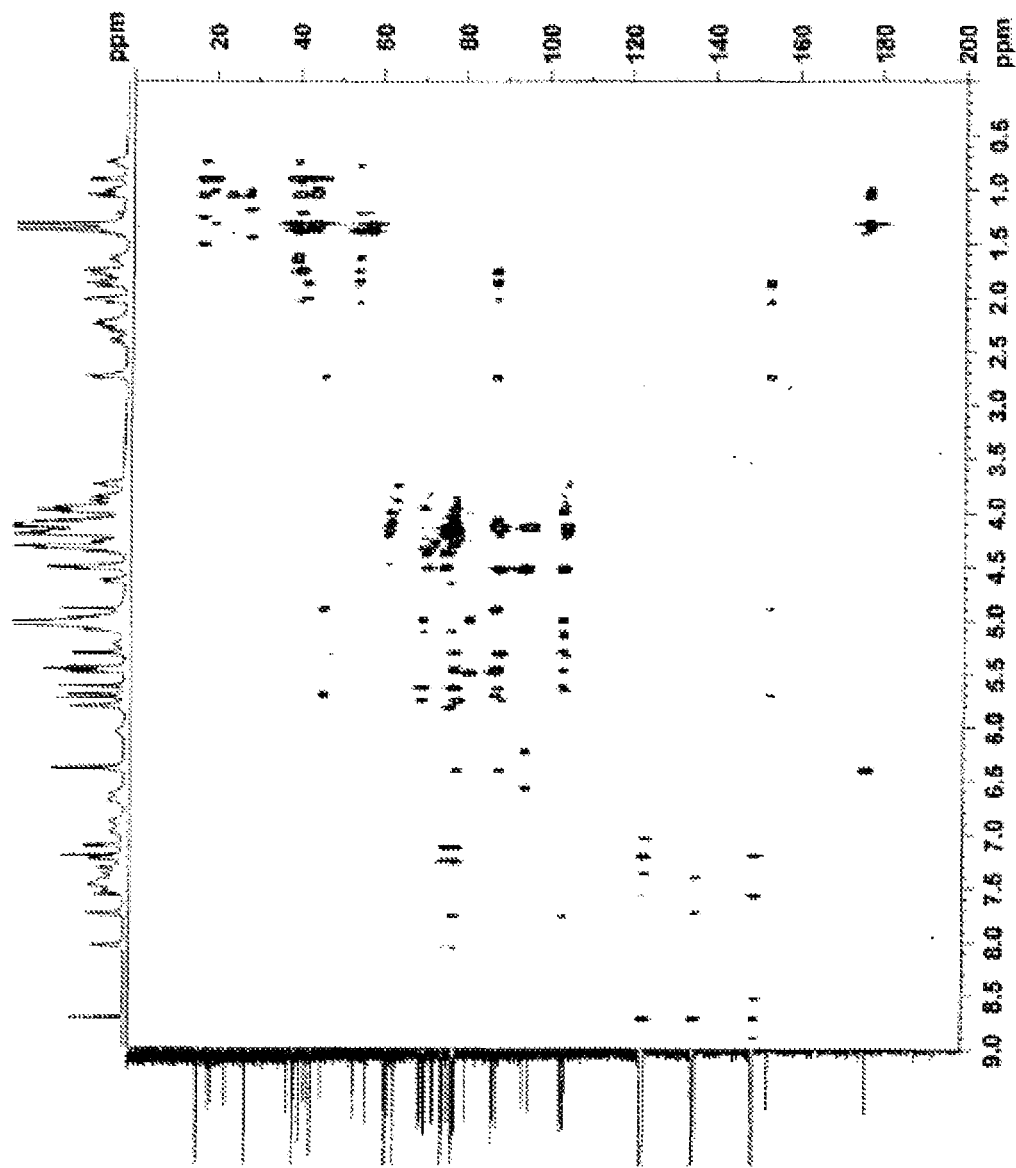
FIG. 4: illustrates the HMBC spectrum of Reb X (600 MHz, $C_5D_5N$).

Recently, rebaudioside X, 13-[(2-O-β-D-glucopyranosyl-3-O-β-D-glucopyranosyl-β-D-glucopyranosyl)oxy]ent kaur-16-en-19-oic acid-[(2-O-β-D -glucopyranosyl-3-O-β-D-glucopyranosyl-β-D-glucopyranosyl)ester], was isolated from *Stevia rebaudiana* and characterized:

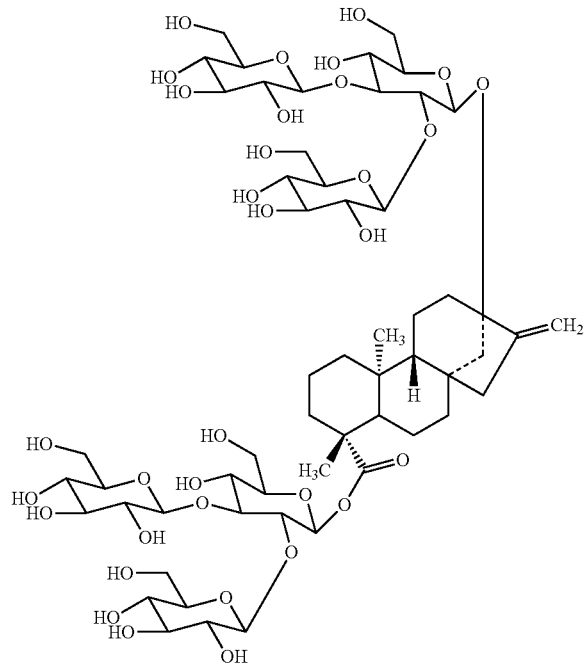

Rebaudioside X is present in minute quantities in *Stevia rebaudiana*, about 0.05-0.5% by weight. Methods of isolating rebaudioside X have been disclosed in the co-pending application PCT/US2012/070562, the contents of which are incorporated herein by reference.

Rebaudioside X (also referred to as rebaudioside M) is also commercially available from Chromadex.

The present invention is based on the discovery that rebaudioside X acts as a sweetness enhancer when used in certain concentrations in compositions, e.g. beverages, containing traditional caloric sweeteners. Therefore, the present invention allows for the reduction of the amount of caloric sweetener(s) used in said compositions.

I. Definitions

The term "sweetness recognition threshold," as generally used herein, is the lowest known concentration of a sweet compound that is perceivable by the human sense of taste. As such, rebaudioside X enhances or potentiates the sweet taste of sweeteners without providing any noticeable sweet taste by itself when present below its sweetness recognition threshold concentration. However, rebaudioside X may provide a detectable sweet taste at concentrations above its sweetness recognition threshold. The sweetness recognition threshold of rebaudioside X is about 20 to about 30 ppm.

The term "isosweet," as used herein, refers to compositions that have equivalent sweetness. Generally, the sweetness of a given composition is typically measured with reference to a solution of sucrose. See "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Carr, and L. M. Brands, in Sweeteners: Discovery, Molecular Design and Chemoreception, D. E. Walters, F. T. Orthoefer, and G. E. DuBois, Eds., American Chemical Society, Washington, D.C. (1991), pp 261-276.

The term "sucrose equivalence," as used herein, refers to the sweetness of a composition containing at least one non-sucrose sweetener against a sucrose reference. Typically, taste panelists are trained to detect sweetness of reference sucrose solutions containing between 1-15% sucrose (w/v). Other non-sucrose sweeteners are then tasted at a series of dilutions to determine the concentration of the non-sucrose, i.e. rebaudioside X, sweetener that is as sweet (i.e. isosweet) to a given percent sucrose reference.

For example, if a 1% solution of a sweetener composition containing a carbohydrate sweetener and rebaudioside X is as sweet as a 10% sucrose solution, then the sweetener composition is said to be 10 times as potent as sucrose, and has 10% sucrose equivalence.

II. Compositions

A. Sweetened Compositions

In one embodiment, the present invention provides a sweetened composition comprising at least one sweetener and rebaudioside X. The at least one sweetener, which is not rebaudioside X, is present in a concentration above the sweetness recognition threshold. In contrast, rebaudioside X is present in the sweetened composition in a concentration at or below its sweetness recognition threshold. The sweetness recognition threshold of rebaudioside X is about 20-30 ppm, which is sufficient to provide about a sucrose equivalence of about 1.0-1.5%.

Rebaudioside X, when present in the sweetened composition in a concentration at or below the sweetness recognition threshold, enhances the sweetness of a sweetened composition by an amount more than the detectable sweetness of a solution containing the same concentration of rebaudioside X (in the absence of any additional sweeteners). In other words, the increase in isosweetness of a sweetened composition containing rebaudioside X in an amount at or below its sweetness recognition threshold concentration compared to the same sweetened composition in the absence of rebaudioside X is greater than the isosweetness of a solution of rebaudioside X (in the absence of any additional sweeteners).

As an example, a solution containing 20 ppm rebaudioside X was found to be isosweet to a 1.0% (w/v) sucrose solution. A beverage containing 7.0% (w/v) sucrose and 20 ppm rebaudioside X was isosweet to a 9.5% (w/v) sucrose solution. Accordingly, the increase in isosweetness provided by the 20 ppm rebaudioside X (2.5% (w/v)) is greater than the sweetness of 20 ppm rebaudioside X alone (1.0% (w/v)). Therefore, it can be said that the effect of rebaudioside X is not merely additive to the sucrose in the beverage (if that were the case, one would expect an isosweetness of 8.0% (w/v)), but rather is acting to enhance the detected sweetness of the sucrose in beverage.

In one embodiment, rebaudioside X enhances the sweetness of the sweetened composition by about 1.0% (w/v) sucrose equivalence or greater. The rebaudioside X enhances the sweetness of the sweetened composition from about 1.0% to about 3.0% (w/v) sucrose equivalence, such as, for example, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9% or about 3.0% sucrose equivalence.

In another particular embodiment, rebaudioside X enhances the sweetness of the sweetened composition by about 1.5% (w/v) sucrose equivalence or greater. The rebaudioside X enhances the sweetness of the sweetened composition from about 1.5% to about 3.0% (w/v) sucrose equivalence, such as, for example, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9% or about 3.0% sucrose equivalence.

The rebaudioside X can be provided as a purified material (e.g. 100% pure) or as part of a *Stevia* extract or mixture of steviol glycosides. In one embodiment, rebaudioside X is from about 80% to about 99% pure, that is, rebaudioside X comprises about 80% to about 99% by weight in a *Stevia* extract or steviol glycoside mixture. In a particular embodiment, rebaudioside X is about 95% pure.

Moreover, the form of rebaudioside X can be polymorphic, amorphous or a combination thereof. In one embodiment, the rebaudioside X is Form A rebaudioside X. In another embodiment, the rebaudioside X is amorphous rebaudioside X. Furthermore the rebaudioside X can be spray-dried.

The sweetener in the sweetened composition may be any caloric or non-caloric, natural or synthetic sweetener. In a preferred embodiment, the sweetener is a caloric sweetener.

In one embodiment, the sweetener is a carbohydrate sweetener. Non-limiting examples of suitable carbohydrate sweeteners include sucrose, fructose, glucose, erythritol, maltitol, lactitol, sorbitol, mannitol, xylitol, tagatose, trehalose, leucrose, galactose, rhamnose, cyclodextrin (e.g., α-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligosaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, isomerized liquid sugars such as high fructose corn/starch syrup (HFCS/HFSS) (e.g., HFCS55, HFCS42, or HFCS90), coupling sugars, soybean oligosaccharides, glucose syrup and combinations thereof.

In a particular embodiment, the sweetener is a carbohydrate sweetener selected from the group consisting of glucose, fructose, sucrose, high fructose corn syrup and combinations thereof.

In another particular embodiment, the carbohydrate sweetener is a rare sugar selected from the group consisting of D-psicose, D-allose, D-turanose, D-tagatose, D-trehalose, D-leucrose and combinations thereof.

In yet other embodiments, the sweetener is a synthetic sweetener. As used herein, the phrase "synthetic sweetener" refers to any composition which is not found naturally in nature and characteristically has a sweetness potency greater than sucrose, fructose, or glucose, yet has less calories. Non-limiting examples of synthetic high-potency sweeteners suitable for embodiments of this disclosure include sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In still other embodiments, the sweetener can be a natural high potency sweetener that is not rebaudioside X. Suitable natural high potency sweeteners include, but are not limited to, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, dulcoside A, dulcoside B, rubusoside, *stevia*, steviosides, mogroside IV, mogroside V, Luo Han Guo sweetener, siamenoside, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobtain, baiyunoside, osladin, polypodoside A, pterocaryoside A, pterocaryoside B, mukurozioside, phlomisoside I, periandrin I, abrusoside A, steviolbioside and cyclocarioside I. The natural high potency sweetener can be provided as a pure compound or, alternatively, as part of an extract.

The sweetened compositions can have any concentration of sweetener described herein. In some embodiments, the sweetened composition has a sweetener concentration of at least about 2% (w/v), such as, for example, from about 2% to about 15%, or from about 5% to about 12%.

In one embodiment, a sweetened composition comprises rebaudioside X having greater than about 95% purity and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup and/or a combination thereof, wherein the at least one sweetener is present in a concentration above the sweetness recognition threshold concentration, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any additional sweeteners).

In a particular embodiment, a sweetened composition comprises rebaudioside X having a purity greater than about 95% and sucrose, wherein sucrose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and fructose, wherein fructose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and glucose, wherein glucose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and high fructose corn syrup, wherein high fructose corn syrup is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and D-psicose, wherein D-psicose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and D-allose, wherein D-allose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and D-turanose, wherein D-turanose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and D-tagatose, wherein D-tagatose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and D-trehalose, wherein D-trehalose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and D-leucrose, wherein D-leucrose is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In another particular embodiment, a sweetened composition comprises rebaudioside X having a purity greater than about 95% and rare sugar syrup, wherein rare sugar syrup is present in a concentration above the sweetness recognition threshold, wherein the rebaudioside X is present in a concentration at or below the sweetness recognition threshold, and wherein the rebaudioside X enhances the sweetness of said sweetened composition by an amount more than the detectable sweetness of a solution containing the same concentration of rebaudioside X (in the absence of any other sweetener).

In one embodiment, a sweetened composition comprises rebaudioside X having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence.

In a more particular embodiment, a sweetened composition comprises rebaudioside X having a purity greater than about 95% and sucrose, wherein sucrose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% (w/v) to about 3.0% (w/v) sucrose equivalence.

In another particular embodiment, a sweetened composition comprises rebaudioside X having a purity greater than about 95% and fructose, wherein fructose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and glucose, wherein glucose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and high fructose corn syrup, wherein high fructose corn syrup is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and D-psicose, wherein D-psicose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and D-allose, wherein D-allose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and D-turanose, wherein D-turanose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and D-tagatose, wherein D-tagatose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and D-trehalose, wherein D-trehalose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and D-leucrose, wherein D-leucrose is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

In another particular embodiment, a sweetened composition comprises rebaudioside X having a purity greater than about 95% and rare sugar syrup, wherein rare sugar syrup is present in a concentration above the sweetness recognition threshold concentration, wherein the rebaudioside X is present in a concentration at or below the sweetness recognition threshold, and wherein the rebaudioside X enhances the sweetness of the sweetened composition by at least about 1.0% (w/v) sucrose equivalence. In a more particular embodiment, the rebaudioside X enhances the sweetness of the sweetened composition from about 1.0% to about 3.0% (w/v) sucrose equivalence.

The sweetened composition can be any edible or oral composition suitable for use in the mouth or ingestion. Exemplary sweetened compositions include, for example, pharmaceutical compositions, edible gel mixes and compositions, dental compositions, foodstuffs (confections, condiments, chewing gum, cereal compositions, baked goods, dairy products, and tabletop sweetener compositions), beverages and beverage products.

The sweetened composition can further contain one or more functional ingredients, detailed below. Functional ingredients include, but are not limited to, vitamins, minerals, antioxidants, preservatives, glucosamine, polyphenols and combinations thereof. Any suitable functional ingredient described herein can be used.

The sweetened composition can further contain one or more additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

1. Beverages

In a particular embodiment, the sweetened composition is a beverage.

As used herein, a "beverage" is a ready-to-drink beverage. Suitable ready-to-drink beverages include carbonated and non-carbonated beverages. Carbonated beverages include, but are not limited to, soft drinks, cola, lemon-lime flavored sparkling beverage, orange flavored sparkling beverage, grape flavored sparkling beverage, strawberry flavored sparkling beverage, pineapple flavored sparkling beverage, ginger-ale, soft drinks, root beer and malt beverages.

Non-carbonated beverages include, but are not limited to fruit juice, fruit-flavored juice, juice drinks, nectars, vegetable juice, vegetable-flavored juice, sports drinks, energy drinks, protein drinks, enhanced water with vitamins, near water drinks (e.g., water with natural or synthetic flavorants), coconut water, tea type (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverages contain a liquid matrix, i.e. the basic ingredient in which the ingredients—including the sweetener and rebaudioside X of the present invention—are dissolved. In one embodiment, the liquid matrix is water of beverage quality, such as, for example deionized water, distilled water, reverse osmosis water, carbon-treated water, purified water, demineralized water and combinations thereof, can be used. Additional suitable liquid matrices include, but are not limited to phosphoric acid, phosphate buffer, citric acid, citrate buffer and carbon-treated water.

In one embodiment, the beverage contains inclusions, i.e. pulp, seed, chunks, etc.

Carbohydrate sweeteners can be present in the beverage in a concentration from about 100 ppm to about 140,000 ppm. Rare sugars can be present in the beverage in a concentration from about 50 ppm to about 100,000 ppm. Synthetic sweeteners may be present in the beverage in a concentration from about 0.3 ppm to about 3,500 ppm. Natural high potency sweeteners may be preset in the beverage in a concentration from about 0.1 ppm to about 3,000 ppm.

The beverage can further include additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

In one embodiment, the polyol can be present in the beverage in a concentration from about 100 ppm to about 250,000 ppm, such as, for example, from about 5,000 ppm to about 40,000 ppm.

In another embodiment, the amino acid can be present in the beverage in a concentration from about 10 ppm to about 50,000 ppm, such as, for example, from about 1,000 ppm to about 10,000 ppm, from about 2,500 ppm to about 5,000 ppm or from about 250 ppm to about 7,500 ppm.

In still another embodiment, the nucleotide can be present in the beverage in a concentration from about 5 ppm to about 1,000 ppm.

In yet another embodiment, the organic acid additive can be present in the beverage in a concentration from about 10 ppm to about 5,000 ppm.

In yet another embodiment, the inorganic acid additive can be present in the beverage in a concentration from about 25 ppm to about 25,000 ppm.

In still another embodiment, the bitter compound can be present in the beverage in a concentration from about 25 ppm to about 25,000 ppm.

In yet another embodiment, the flavorant can be present in the beverage a concentration from about 0.1 ppm to about 5,000 ppm.

In a still further embodiment, the polymer can be present in the beverage in a concentration from about 30 ppm to about 2,000 ppm.

In another embodiment, the protein hydrosylate can be present in the beverage in a concentration from about 200 ppm to about 50,000.

In yet another embodiment, the surfactant additive can be present in the beverage in a concentration from about 30 ppm to about 2,000 ppm.

In still another embodiment, the flavonoid additive can be present in the beverage a concentration from about 0.1 ppm to about 1,000 ppm.

In yet another embodiment, the alcohol additive can be present in the beverage in a concentration from about 625 ppm to about 10,000 ppm.

In a still further embodiment, the astringent additive can be present in the beverage in a concentration from about 10 ppm to about 5,000 ppm.

The beverage can further contain one or more functional ingredients, detailed below. Functional ingredients include, but are not limited to, vitamins, minerals, antioxidants, preservatives, glucosamine, polyphenols and combinations thereof. Any suitable functional ingredient described herein can be used.

It is contemplated that the pH of the beverage does not materially or adversely affect the sweetness enhancement. A non-limiting example of the pH range of the beverage may be from about 1.8 to about 10. A further example includes a pH range from about 2 to about 5. In a particular embodiment, the pH of beverage can be from about 2.5 to about 4.2. One of skill in the art will understand that the pH of the beverage can vary based on the type of beverage. Dairy beverages, for example, can have pHs greater than 4.2.

The titratable acidity of the beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of the beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, a beverage comprises a carbohydrate sweetener and between about 20-30 ppm rebaudioside X, wherein the liquid matrix of the beverage is selected from the group consisting of water, phosphoric acid, phosphate buffer, citric acid, citrate buffer, carbon-treated water and combinations thereof. The pH of the beverage can be from about 2.5 to about 4.2. The beverage can further include additives, such as, for example, erythritol. The beverage can further include functional ingredients, such as vitamins.

In one embodiment, a beverage comprises at least one sweetener and rebaudioside X having a purity greater than about 95%, wherein the at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof is present in a concentration above its sweetness recognition threshold, wherein rebaudioside X is present in a concentration at or below its sweetness recognition threshold, and wherein rebaudioside X enhances the sweetness of the beverage by an amount more than the detectable sweetness of a solution containing the same concentration of rebaudioside X in the absence of the at least one sweetener.

In another embodiment, a beverage comprises rebaudioside X having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof, wherein the at least one sweetener is present in a concentration above the sweetness recognition threshold concentration, wherein the rebaudioside X is present in a concentration at or below the sweetness recognition threshold, and wherein the rebaudioside X enhances the sweetness of the beverage by at least about 1.0% (w/v) sucrose equivalence, such as, for example, from about 1.0% to about 3.0%.

In one embodiment, a reduced-calorie soda comprises, for example, caramel color, phosphoric acid, sugar (i.e. sucrose, HFCS or HFSS), rebaudioside X, potassium benzoate, natural colors, citric acid, and caffeine.

In another embodiment, a reduced-calorie soda comprises, for example, caramel color, phosphoric acid, sugar, erythritol, rebaudioside X, potassium benzoate, natural colors, citric acid, and caffeine.

In still another embodiment, a reduced-calorie soda comprises, for example, caramel color, phosphoric acid, sugar, erythritol, D-tagatose, rebaudioside X, potassium benzoate, natural colors, citric acid, and caffeine.

In yet another embodiment, a reduced-calorie soda comprises, for example, caramel color, phosphoric acid, sugar, D-tagatose, rebaudioside X, potassium benzoate, natural colors, citric acid, and caffeine.

In one embodiment, a reduced-calorie soda comprises, for example, caramel color, phosphoric acid, sugar, D-psicose, rebaudioside X, potassium benzoate, natural colors, citric acid, and caffeine.

In another embodiment, a reduced-calorie lemon-lime carbonated soft drink comprises, for example, sugar, rebaudioside X, natural flavors, citric acid, sodium citrate, sodium benzoate, malic acid and *Stevia* leaf extract.

In still another embodiment, a half-calorie lemon-lime carbonated soft drink comprises, for example, sugar, erythritol, rebaudioside X, natural flavors, citric acid, malic acid, sodium citrate, sodium benzoate and *Stevia* leaf extract.

In one embodiment, a reduced-calorie orange-flavored carbonated soft drink comprises, for example, sugar, rebaudioside X, natural flavors, citric acid, modified food starch, sodium hexametaphosphate, glycerol ester of rosin, yellow 6, sodium benzoate, *stevia* leaf extract, brominated vegetable oil and red 40.

In another embodiment, a reduced-calorie citrus-flavored carbonated soft drink comprises, for example, sugar, rebaudioside X, natural flavors, citric acid, potassium citrate, concentrated grape fruit juice, potassium sorbate, potassium benzoate, EDTA, acacia, glycerol ester of rosin, brominated vegetable oil and carob bean gum.

In another embodiment, a reduced-calorie sports drink comprises, for example, rebaudioside X, citric acid, salt, monopotassium phosphate, magnesium chloride, calcium chloride, natural flavors, sugar, vitamins B3, B6, B12, blue 1, ascorbic acid, and calcium disodium EDTA.

In still another embodiment, a reduced-calorie spicy cherry carbonated soft drink comprises, for example, rebaudioside X, sugar caramel color, phosphoric acid, potassium sorbate, potassium benzoate, artificial and natural flavors, caffeine, monosodium phosphate, lactic acid, and polyethylene glycol.

In yet another embodiment, an enhanced water beverage comprises, for example, rebaudioside X, erythritol, sugar, magnesium and calcium lactate, potassium phosphate, citric acid, natural flavors, vitamin C (ascorbic acid), phosphoric acid, calcium phosphate, vitamins B3, E, B5, B6, B12, zinc gluconate and vitamin A palmitate Use of rebaudioside X in a concentration at or below its sweetness recognition threshold in a beverage containing a sweetener in a concentration above its sweetness recognition threshold means less caloric sweetener is required to provide the same sucrose equivalence. Accordingly, the amount of caloric sweetener in a beverage can be reduced by about 15% to about 20%, while providing the same sucrose equivalence.

Use of rebaudioside X in a concentration at or below its sweetness recognition threshold in a beverage containing a sweetener in a concentration above its sweetness recognition threshold can provide a reduced calorie beverage with a sucrose equivalence from about 7.5% to about 10.0% (w/v), where the amount of sucrose in the beverage is less than would normally be used to provide a 7.5%-10.0% (w/v) sucrose solution (in the absence of any additional sweeteners).

2. Other Sweetened Compositions
Pharmaceutical Compositions

In one embodiment, the sweetened composition is a pharmaceutical composition. The pharmaceutical composition may be in the form of a syrup, an emulsion, a suspension, a solution, or any other liquid form for providing the pharmaceutical composition to a patient. In particular embodiments, the pharmaceutical composition may be in a form for oral administration, buccal administration, sublingual administration, or any other route of administration as known in the art.

As referred to herein, "pharmaceutically active substance" means any drug, drug formulation, medication, prophylactic agent, therapeutic agent, or other substance having biological activity. As referred to herein, "excipient material" refers to any inactive substance used as a vehicle for an active ingredient, such as any material to facilitate handling, stability, dispersibility, wettability, and/or release kinetics of a pharmaceutically active substance.

Suitable pharmaceutically active substances include, but are not limited to, medications for the gastrointestinal tract or digestive system, for the cardiovascular system, for the central nervous system, for pain or consciousness, for musculo-skeletal disorders, for the ear, for the ear, nose and oropharynx, for the respiratory system, for endocrine problems, for the reproductive system or urinary system, for contraception, for obstetrics and gynecology, for the skin, for infections and infestations, for immunology, for allergic disorders, for nutrition, for neoplastic disorders, for diagnostics, for euthanasia, or other biological functions or disorders. Examples of suitable pharmaceutically active substances for embodiments of the present invention include, but are not limited to, antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, anti-inflammatories, anti-gluacoma drugs, sympathomimetics, steroids, ceruminolytics, bronchodilators, NSAIDS, antitussive, mucolytics, decongestants, corticosteroids, androgens, antiandrogens, gonadotropins, growth hormones, insulin, antidiabetics, thyroid hormones, calcitonin, diphosphonates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarials, anthelmintics, antiprotozoal, antiserums, vaccines, interferons, tonics, vitamins, cytotoxic drugs, sex hormones, aromatase inhibitors, somatostatin inhibitors, or similar type substances, or combinations thereof. Such components generally are recognized as safe (GRAS) and/or are U.S. Food and Drug Administration (FDA)-approved.

The pharmaceutically active substance is present in the pharmaceutical composition in widely ranging amounts depending on the particular pharmaceutically active agent being used and its intended applications. An effective dose of any of the herein described pharmaceutically active substances can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular pharmaceutically active agent administered; the mode of administration; the bioavailability characteristic of the preparation administered; the dose regimen selected; and the use of concomitant medication. The pharmaceutically active substance is included in the pharmaceutically acceptable carrier, diluent, or excipient in an amount sufficient to deliver to a patient a therapeutic amount of the pharmaceutically active substance in vivo in the absence of serious toxic effects when used in generally acceptable amounts. Thus, suitable amounts can be readily discerned by those skilled in the art.

According to particular embodiments of the present invention, the concentration of pharmaceutically active substance in the pharmaceutical composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimes should be adjusted over time according to the individual need and the professional judgment of the person administering or supervising the administration of the pharmaceutical compositions, and that the dosage ranges set forth herein are exemplary only and are not intended to limit the scope or practice of the claimed composition. The pharmaceutically active substance may be administered at once, or may be divided into a number of smaller doses to be administered at varying intervals of time.

The pharmaceutical composition also may comprise other pharmaceutically acceptable excipient materials. Examples of suitable excipient materials for embodiments of this invention include, but are not limited to, antiadherents, binders (e.g., microcrystalline cellulose, gum tragacanth, or gelatin), coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof. For example, the pharmaceutical compositions of the present invention may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

The excipient material of the pharmaceutical composition may optionally include other artificial or natural sweeteners, bulk sweeteners, or combinations thereof. Bulk sweeteners include both caloric and non-caloric compounds. In a particular embodiment, the additive functions as the bulk sweetener. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the pharmaceutical composition in widely ranging amounts depending on the degree of sweetness desired. Suitable amounts of both sweeteners would be readily discernible to those skilled in the art.

Edible Gel Mixes and Edible Gel Compositions

In one embodiment, the sweetened composition is an edible gel or edible gel mix.

Edible gels are gels that can be eaten. A gel is a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives.

Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Non-limiting examples of fluids for use in particular embodiments include water, dairy fluids, dairy analogue fluids, juices, alcohol, alcoholic beverages, and combinations thereof. Non-limiting examples of dairy fluids which may be used in particular embodiments include milk, cultured milk, cream, fluid whey, and mixtures thereof. Non-limiting examples of dairy analogue fluids which may be used in particular embodiments include, for example, soy milk and non-dairy coffee whitener. Because edible gel products found in the marketplace typically are sweetened with sucrose, it is desirable to sweeten edible gels with an alternative sweetener in order provide a low-calorie or non-calorie alternative.

As used herein, the term "gelling ingredient" denotes any material that can form a colloidal system within a liquid medium. Non-limiting examples of gelling ingredients for use in particular embodiments include gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, such as the particular gelling ingredient used, the particular fluid base used, and the desired properties of the gel.

Non-limiting examples of other ingredients for use in particular embodiments include a food acid, a salt of a food acid, a buffering system, a bulking agent, a sequestrant, a cross-linking agent, one or more flavors, one or more colors, and combinations thereof. Non-limiting examples of food acids for use in particular embodiments include citric acid, adipic acid, fumaric acid, lactic acid, malic acid, and combinations thereof. Non-limiting examples of salts of food acids for use in particular embodiments include sodium salts of food acids, potassium salts of food acids, and combinations thereof. Non-limiting examples of bulking agents for use in particular embodiments include raftilose, isomalt, sorbitol, polydextrose, maltodextrin, and combinations thereof. Non-limiting examples of sequestrants for use in particular embodiments include calcium disodium ethylene tetra-acetate, glucono delta-lactone, sodium gluconate, potassium gluconate, ethylenediaminetetraacetic acid (EDTA), and combinations thereof. Non-limiting examples of cross-linking agents for use in particular embodiments include calcium ions, magnesium ions, sodium ions, and combinations thereof.

Dental Compositions

In one embodiment, the sweetened composition is a dental composition.

The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, and the like, for example.

As referred to herein, "active dental substance" means any composition which can be used to improve the aesthetic appearance and/or health of teeth or gums or prevent dental caries. As referred to herein, "base material" refers to any inactive substance used as a vehicle for an active dental substance, such as any material to facilitate handling, stability, dispersibility, wettability, foaming, and/or release kinetics of an active dental substance.

Suitable active dental substances for embodiments of this invention include, but are not limited to, substances which remove dental plaque, remove food from teeth, aid in the elimination and/or masking of halitosis, prevent tooth decay, and prevent gum disease (i.e., Gingiva). Examples of suitable active dental substances for embodiments of the present invention include, but are not limited to, anticaries drugs, fluoride, sodium fluoride, sodium monofluorophosphate, stannos fluoride, hydrogen peroxide, carbamide peroxide (i.e., urea peroxide), antibacterial agents, plaque removing agents, stain removers, anticalculus agents, abrasives, baking soda, percarbonates, perborates of alkali and alkaline earth metals, or similar type substances, or combinations thereof. Such components generally are recognized as safe (GRAS) and/or are U.S. Food and Drug Administration (FDA)-approved.

According to particular embodiments of the invention, the active dental substance is present in the dental composition in an amount ranging from about 50 ppm to about 3000 ppm of the dental composition. Generally, the active dental substance is present in the dental composition in an amount effective to at least improve the aesthetic appearance and/or health of teeth or gums marginally or prevent dental caries. For example, a dental composition comprising a toothpaste may include an active dental substance comprising fluoride in an amount of about 850 to 1,150 ppm.

The dental composition also may comprise other base materials. Examples of suitable base materials for embodiments of this invention include, but are not limited to, water, sodium lauryl sulfate or other sulfates, humectants, enzymes, vitamins, herbs, calcium, flavorings (e.g., mint, bubblegum, cinnamon, lemon, or orange), surface-active agents, binders, preservatives, gelling agents, pH modifiers, peroxide activators, stabilizers, coloring agents, or similar type materials, and combinations thereof.

The base material of the dental composition may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof.

Generally, the amount of bulk sweetener present in the dental composition ranges widely depending on the particular embodiment of the dental composition and the desired degree of sweetness. Those of ordinary skill in the art will readily ascertain the appropriate amount of bulk sweetener. In particular embodiments, the bulk sweetener is present in the dental composition in an amount in the range of about 0.1 to about 5 weight percent of the dental composition.

According to particular embodiments of the invention, the base material is present in the dental composition in an amount ranging from about 20 to about 99 percent by weight of the dental composition. Generally, the base material is present in an amount effective to provide a vehicle for an active dental substance.

Generally, the amount of the sweetener varies widely depending on the nature of the particular dental composition and the desired degree of sweetness. Those skilled in the art will be able to discern a suitable amount of sweetener for such dental composition.

Foodstuffs include, but are not limited to, confections, condiments, chewing gum, cereal, baked goods, and dairy products.

Confections

In one embodiment, the sweetened composition is a confection.

As referred to herein, "confection" can mean a sweet, a lollie, a confectionery, or similar term. The confection generally contains a base composition component and a sweetener component. The confection may be in the form of any food that is typically perceived to be rich in sugar or is typically sweet. According to particular embodiments of the present invention, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e.g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e.g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible natural synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; crémes including butter crémes, flour pastes, whipped cream and the like; jams including strawberry jam, marmalade and the like; and breads including sweet breads and the like or other starch products, and combinations thereof.

As referred to herein, "base composition" means any composition which can be a food item and provides a matrix for carrying the sweetener component.

Suitable base compositions for embodiments of this invention may include flour, yeast, water, salt, butter, eggs, milk, milk powder, liquor, gelatin, nuts, chocolate, citric acid, tartaric acid, fumaric acid, natural flavors, artificial flavors, colorings, polyols, sorbitol, isomalt, maltitol, lactitol, malic acid, magnesium stearate, lecithin, hydrogenated glucose syrup, glycerine, natural or synthetic gum, starch, and the like, and combinations thereof. Such components generally are recognized as safe (GRAS) and/or are U.S. Food and Drug Administration (FDA)-approved. According to particular embodiments of the invention, the base composition is present in the confection in an amount ranging from about 0.1 to about 99 weight percent of the confection.

The base composition of the confection may optionally include other artificial or natural sweeteners, bulk sweeteners, or combinations thereof. Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. Generally, the amount of bulk sweetener present in the confection ranges widely depending on the particular embodiment of the confection and the desired degree of sweetness. Those of ordinary skill in the art will readily ascertain the appropriate amount of bulk sweetener.

In a particular embodiment, a confection comprises a non-rebaudioside X sweetener, rebaudioside X and a base composition. Those of ordinary skill in the art will readily ascertain the appropriate amount of non-rebaudioside X sweetener. In a particular embodiment, the non-rebaudioside X sweetener is present in the confection in an amount in the range of about 30 ppm to about 6000 ppm of the confection.

Condiment Compositions

In one embodiment, the sweetened composition is a condiment.

Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

Condiment bases generally comprise a mixture of different ingredients, non-limiting examples of which include vehicles (e.g., water and vinegar); spices or seasonings (e.g., salt, pepper, garlic, mustard seed, onion, paprika, turmeric, and combinations thereof); fruits, vegetables, or their products (e.g., tomatoes or tomato-based products (paste, puree), fruit juices, fruit juice peels, and combinations thereof); oils or oil emulsions, particularly vegetable oils; thickeners (e.g., xanthan gum, food starch, other hydrocolloids, and combinations thereof); and emulsifying agents (e.g., egg yolk solids, protein, gum arabic, carob bean gum, guar gum, gum karaya, gum tragacanth, carageenan, pectin, propylene glycol esters of alginic acid, sodium carboxymethyl-cellulose, polysorbates, and combinations thereof). Recipes for condiment bases and methods of making condiment bases are well known to those of ordinary skill in the art.

Generally, condiments also comprise caloric sweeteners, such as sucrose, high fructose corn syrup, molasses, honey, or brown sugar. In exemplary embodiments of the condiments provided herein, rebaudioside X is used in addition to traditional caloric sweeteners. Accordingly, a condiment composition desirably comprises rebaudioside X, a caloric sweetener and a condiment base.

The condiment composition optionally may include other natural and/or synthetic high-potency sweeteners, bulk sweeteners, pH modifying agents (e.g., lactic acid, citric acid, phosphoric acid, hydrochloric acid, acetic acid, and combinations thereof), fillers, functional agents (e.g., pharmaceutical agents, nutrients, or components of a food or plant), flavorings, colorings, or combinations thereof.

Chewing Gum Compositions

In one embodiment, the sweetened composition is a chewing gum composition. Chewing gum compositions generally comprise a water-soluble portion and a water-insoluble chewable gum base portion. The water soluble portion, which typically includes the rebaudioside X, dissipates with a portion of the flavoring agent over a period of time during chewing while the insoluble gum base portion is retained in the mouth. The insoluble gum base generally determines whether a gum is considered chewing gum, bubble gum, or a functional gum.

The insoluble gum base, which is generally present in the chewing gum composition in an amount in the range of about 15 to about 35 weight percent of the chewing gum composition, generally comprises combinations of elastomers, softeners (plasticizers), emulsifiers, resins, and fillers. Such components generally are considered food grade, recognized as safe (GRA), and/or are U.S. Food and Drug Administration (FDA)-approved.

Elastomers, the primary component of the gum base, provide the rubbery, cohesive nature to gums and can include one or more natural rubbers (e.g., smoked latex, liquid latex, or guayule); natural gums (e.g., jelutong, perillo, sorva, massaranduba balata, massaranduba chocolate, nispero, rosindinha, chicle, and gutta hang kang); or synthetic elastomers (e.g., butadiene-styrene copolymers, isobutylene-isoprene copolymers, polybutadiene, polyisobutylene, and vinyl polymeric elastomers). In a particular embodiment, the elastomer is present in the gum base in an amount in the range of about 3 to about 50 weight percent of the gum base.

Resins are used to vary the firmness of the gum base and aid in softening the elastomer component of the gum base. Non-limiting examples of suitable resins include a rosin ester, a terpene resin (e.g., a terpene resin from α-pinene, β-pinene and/or d-limonene), polyvinyl acetate, polyvinyl alcohol, ethylene vinyl acetate, and vinyl acetate-vinyl laurate copolymers. Non-limiting examples of rosin esters include a glycerol ester of a partially hydrogenated rosin, a glycerol ester of a polymerized rosin, a glycerol ester of a partially dimerized rosin, a glycerol ester of rosin, a pentaerythritol ester of a partially hydrogenated rosin, a methyl ester of rosin, or a methyl ester of a partially hydrogenated rosin. In a particular embodiment, the resin is present in the gum base in an amount in the range of about 5 to about 75 weight percent of the gum base.

Softeners, which also are known as plasticizers, are used to modify the ease of chewing and/or mouthfeel of the chewing gum composition. Generally, softeners comprise oils, fats, waxes, and emulsifiers. Non-limiting examples of oils and fats include tallow, hydrogenated tallow, large, hydrogenated or partially hydrogenated vegetable oils (e.g., soybean, canola, cottonseed, sunflower, palm, coconut, corn, safflower, or palm kernel oils), cocoa butter, glycerol monostearate, glycerol triacetate, glycerol abietate, leithin, monoglycerides, diglycerides, triglycerides acetylated monoglycerides, and free fatty acids. Non-limiting examples of waxes include polypropylene/polyethylene/Fisher-Tropsch waxes, paraffin, and microcrystalline and natural waxes (e.g., candelilla, beeswas and carnauba). Microcrystalline waxes, especially those with a high degree of crystallinity and a high melting point, also may be considered as bodying agents or textural modifiers. In a particular embodiment, the softeners are present in the gum base in an amount in the range of about 0.5 to about 25 weight percent of the gum base.

Emulsifiers are used to form a uniform dispersion of the insoluble and soluble phases of the chewing gum composition and also have plasticizing properties. Suitable emulsifiers include glycerol monostearate (GMS), lecithin (Phosphatidyl choline), polyglycerol polyricinoleic acid (PPGR), mono and diglycerides of fatty acids, glycerol distearate, tracetin, acetylated monoglyceride, glycerol triactetate, and magnesium stearate. In a particular embodiment, the emulsifiers are present in the gum base in an amount in the range of about 2 to about 30 weight percent of the gum base.

The chewing gum composition also may comprise adjuvants or fillers in either the gum base and/or the soluble portion of the chewing gum composition. Suitable adjuvants and fillers include lecithin, inulin, polydextrin, calcium carbonate, magnesium carbonate, magnesium silicate, ground limestome, aluminum hydroxide, aluminum silicate, talc, clay, alumina, titanium dioxide, and calcium phosphate. In particular embodiments, lecithin can be used as an inert filler to decrease the stickiness of the chewing gum composition. In other particular embodiments, lactic acid copolymers, proteins (e.g., gluten and/or zein) and/or guar can be used to create a gum that is more readily biodegradable. The adjuvants or fillers are generally present in the gum base in an amount up to about 20 weight percent of the gum base. Other optional ingredients include coloring agents, whiteners, preservatives, and flavors.

In particular embodiments of the chewing gum composition, the gum base comprises about 5 to about 95 weight percent of the chewing gum composition, more desirably about 15 to about 50 weight percent of the chewing gum composition, and even more desirably from about 20 to about 30 weight percent of the chewing gum composition.

The soluble portion of the chewing gum composition may optionally include other artificial or natural sweeteners, bulk sweeteners, softeners, emulsifiers, flavoring agents, coloring agents, adjuvants, fillers, functional agents (e.g., pharmaceutical agents or nutrients), or combinations thereof. Suitable examples of softeners and emulsifiers are described above.

Bulk sweeteners include both caloric and non-caloric compounds. Non-limiting examples of bulk sweeteners include sucrose, dextrose, maltose, dextrin, dried invert sugar, fructose, high fructose corn syrup, levulose, galactose, corn syrup solids, tagatose, polyols (e.g., sorbitol, mannitol, xylitol, lactitol, erythritol, and maltitol), hydrogenated starch hydrolysates, isomalt, trehalose, and mixtures thereof. In particular embodiments, the bulk sweetener is present in the chewing gum composition in an amount in the range of about 1 to about 75 weight percent of the chewing gum composition.

Flavoring agents may be used in either the insoluble gum base or soluble portion of the chewing gum composition. Such flavoring agents may be natural or artificial flavors. In a particular embodiment, the flavoring agent comprises an essential oil, such as an oil derived from a plant or a fruit, peppermint oil, spearmint oil, other mint oils, clove oil, cinnamon oil, oil of wintergreen, bay, thyme, cedar leaf, nutmeg, allspice, sage, mace, and almonds. In another particular embodiment, the flavoring agent comprises a plant extract or a fruit essence such as apple, banana, watermelon, pear, peach, grape, strawberry, raspberry, cherry, plum, pineapple, apricot, and mixtures thereof. In still another particular embodiment, the flavoring agent comprises a citrus flavor, such as an extract, essence, or oil of lemon, lime, orange, tangerine, grapefruit, citron, or kumquat.

In a particular embodiment, a chewing gum composition comprises rebaudioside X, at least one caloric sweetener and a gum base.

Cereal Compositions

In one embodiment, the sweetened composition is a cereal composition. Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

Cereal compositions generally comprise at least one cereal ingredient. As used herein, the term "cereal ingredient" denotes materials such as whole or part grains, whole or part seeds, and whole or part grass. Non-limiting examples of cereal ingredients for use in particular embodiments include maize, wheat, rice, barley, bran, bran endosperm, bulgur, soghums, millets, oats, rye, triticale, buchwheat, fonio, quinoa, bean, soybean, amaranth, teff, spelt, and kaniwa.

In a particular embodiment, the cereal composition comprises rebaudioside X, at least one caloric sweetener and at least one cereal ingredient. The rebaudioside X may be added to the cereal composition in a variety of ways, such as, for example, as a coating, as a frosting, as a glaze, or as a matrix blend (i.e. added as an ingredient to the cereal formulation prior to the preparation of the final cereal product).

Baked Goods

In one embodiment, the sweetened composition is a baked good. Baked goods, as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Preferred baked goods in accordance with embodiments of this invention can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies, and muffins). Doughs generally are characterized as being flour-based, whereas batters are more water-based.

Baked goods in accordance with particular embodiments of this invention generally comprise a combination of sweetener, water, and fat. Baked goods made in accordance with many embodiments of this invention also contain flour in order to make a dough or a batter. The term "dough" as used herein is a mixture of flour and other ingredients stiff enough to knead or roll. The term "batter" as used herein consists of flour, liquids such as milk or water, and other ingredients, and is thin enough to pour or drop from a spoon. Desirably, in accordance with particular embodiments of the invention, the flour is present in the baked goods in an amount in the range of about 15 to about 60% on a dry weight basis, more desirably from about 23 to about 48% on a dry weight basis.

The type of flour may be selected based on the desired product. Generally, the flour comprises an edible non-toxic flour that is conventionally utilized in baked goods. According to particular embodiments, the flour may be a bleached bake flour, general purpose flour, or unbleached flour. In other particular embodiments, flours also may be used that have been treated in other manners. For example, in particular embodiments flour may be enriched with additional vitamins, minerals, or proteins. Non-limiting examples of flours suitable for use in particular embodiments of the invention include wheat, corn meal, whole grain, fractions of whole grains (wheat, bran, and oatmeal), and combinations thereof. Starches or farinaceous material also may be used as the flour in particular embodiments. Common food starches generally are derived from potato, corn, wheat, barley, oat, tapioca, arrow root, and sago. Modified starches and pregelatinized starches also may be used in particular embodiments of the invention.

The type of fat or oil used in particular embodiments of the invention may comprise any edible fat, oil, or combination thereof that is suitable for baking Non-limiting examples of fats suitable for use in particular embodiments of the invention include vegetable oils, tallow, lard, marine oils, and combinations thereof. According to particular embodiments, the fats may be fractionated, partially hydrogenated, and/or interesterified. In another particular embodiment, the fat desirably comprises reduced, low calorie, or non-digestible fats, fat substitutes, or synthetic fats. In yet another particular embodiment, shortenings, fats, or mixtures of hard and soft fats also may be used. In particular embodiments, shortenings may be derived principally from triglycerides derived from vegetable sources (e.g., cotton seed oil, soybean oil, peanut oil, linseed oil, sesame oil, palm oil, palm kernel oil, rapeseed oil, safflower oil, coconut oil, corn oil, sunflower seed oil, and mixtures thereof). Synthetic or natural triglycerides of fatty acids having chain lengths from 8 to 24 carbon atoms also may be used in particular embodiments. Desirably, in accordance with particular embodiments of this invention, the fat is present in the baked good in an amount in the range of about 2 to about 35% by weight on a dry basis, more desirably from about 3 to about 29% by weight on a dry basis.

Baked goods in accordance with particular embodiments of this invention also comprise water in amounts sufficient to provide the desired consistency, enabling proper forming, machining and cutting of the baked good prior or subsequent to cooking. The total moisture content of the baked good includes any water added directly to the baked good as well as water present in separately added ingredients (e.g., flour, which generally includes about 12 to about 14% by weight moisture). Desirably, in accordance with particular embodiments of this invention, the water is present in the baked good in an amount up to about 25% by weight of the baked good.

Baked goods in accordance with particular embodiments of this invention also may comprise a number of additional conventional ingredients such as leavening agents, flavors, colors, milk, milk by-products, egg, egg by-products, cocoa, vanilla or other flavoring, as well as inclusions such as nuts, raisins, cherries, apples, apricots, peaches, other fruits, citrus peel, preservative, coconuts, flavored chips such a chocolate chips, butterscotch chips, and caramel chips, and combinations thereof. In particular embodiments, the baked goods may also comprise emulsifiers, such as lecithin and monoglycerides.

According to particular embodiments of this invention, leavening agents may comprise chemical leavening agents or yeast leavening agents. Non-limiting examples of chemical leavening agents suitable for use in particular embodiments of this invention include baking soda (e.g., sodium, potassium, or aluminum bicarbonate), baking acid (e.g., sodium aluminum phosphate, monocalcium phosphate, or dicalcium phosphate), and combinations thereof.

In accordance with another particular embodiment of this invention, cocoa may comprise natural or "Dutched" chocolate from which a substantial portion of the fat or cocoa butter has been expressed or removed by solvent extraction, pressing, or other means. In a particular embodiment, it may be necessary to reduce the amount of fat in a baked good comprising chocolate because of the additional fat present in cocoa butter. In particular embodiments, it may be necessary to add larger amounts of chocolate as compared to cocoa in order to provide an equivalent amount of flavoring and coloring.

Baked goods generally also comprise caloric sweeteners, such as sucrose, high fructose corn syrup, erythritol, molasses, honey, or brown sugar. In exemplary embodiments of the baked goods provided herein, the caloric sweetener is supplemented with rebaudioside X. Accordingly, in one embodiment a baked good comprises rebaudioside X, the caloric sweetener(s), fat, water, and optionally flour. In a particular embodiment, the baked good optionally may include other natural and/or synthetic high-potency sweeteners and/or bulk sweeteners.

Dairy Products

In one embodiment, the sweetened composition is a dairy product. Dairy products and processes for making dairy products suitable for use in this invention are well known to those of ordinary skill in the art. Dairy products, as used herein, comprise milk or foodstuffs produced from milk. Non-limiting examples of dairy products suitable for use in embodiments of this invention include milk, milk cream, sour cream, créme fraiche, buttermilk, cultured buttermilk, milk powder, condensed milk, evaporated milk, butter, cheese, cottage cheese, cream cheese, yogurt, ice cream, frozen custard, frozen yogurt, gelato, vla, piima, filmjolk, kajmak, kephir, viili, kumiss, airag, ice milk, casein, ayran, lassi, khoa, or combinations thereof.

Milk is a fluid secreted by the mammary glands of female mammals for the nourishment of their young. The female ability to produce milk is one of the defining characteristics of mammals and provides the primary source of nutrition for newborns before they are able to digest more diverse foods. In particular embodiments of this invention, the dairy products are derived from the raw milk of cows, goats, sheep, horses, donkeys, camels, water buffalo, yaks, reindeer, moose, or humans.

In particular embodiments of this invention, the processing of the dairy product from raw milk generally comprises the steps of pasteurizing, creaming, and homogenizing. Although raw milk may be consumed without pasteurization, it usually is pasteurized to destroy harmful microorganisms such as bacteria, viruses, protozoa, molds, and yeasts. Pasteurizing generally comprises heating the milk to a high temperature for a short period of time to substantially reduce the number of microorganisms, thereby reducing the risk of disease.

Creaming traditionally follows pasteurization step, and involves the separation of milk into a higher-fat cream layer and a lower-fat milk layer. Milk will separate into milk and cream layers upon standing for twelve to twenty-four hours. The cream rises to the top of the milk layer and may be skimmed and used as a separate dairy product. Alternatively, centrifuges may be used to separate the cream from the milk. The remaining milk is classified according to the fat content of the milk, non-limiting examples of which include whole, 2%, 1%, and skim milk.

After removing the desired amount of fat from the milk by creaming, milk is often homogenized. Homogenization prevents cream from separating from the milk and generally involves pumping the milk at high pressures through narrow tubes in order to break up fat globules in the milk. Pasteurization, creaming, and homogenization of milk are common but are not required to produce consumable dairy products. Accordingly, suitable dairy products for use in embodiments of this invention may undergo no processing steps, a single processing step, or combinations of the processing steps described herein. Suitable dairy products for use in embodiments of this invention may also undergo processing steps in addition to or apart from the processing steps described herein.

Particular embodiments of this invention comprise dairy products produced from milk by additional processing steps. As described above, cream may be skimmed from the top of milk or separated from the milk using machine-centrifuges. In a particular embodiment, the dairy product comprises sour cream, a dairy product rich in fats that is obtained by fermenting cream using a bacterial culture. The bacteria produce lactic acid during fermentation, which sours and thickens the cream. In another particular embodiment, the dairy product comprises créme fraiche, a heavy cream slightly soured with bacterial culture in a similar manner to sour cream. Créme fraiche ordinarily is not as thick or as sour as sour cream. In yet another particular embodiment, the dairy product comprises cultured buttermilk. Cultured buttermilk is obtained by adding bacteria to milk. The resulting fermentation, in which the bacterial culture turns lactose into lactic acid, gives cultured buttermilk a sour taste. Although it is produced in a different manner, cultured buttermilk generally is similar to traditional buttermilk, which is a by-product of butter manufacture.

According to other particular embodiments of this invention, the dairy products comprise milk powder, condensed milk, evaporated milk, or combinations thereof. Milk powder, condensed milk, and evaporated milk generally are produced by removing water from milk. In a particular embodiment, the dairy product comprises a milk powder comprising dried milk solids with a low moisture content. In another particular embodiment, the dairy product comprises condensed milk. Condensed milk generally comprises milk with a reduced water content and added sweetener, yielding a thick, sweet product with a long shelf-life. In yet another particular embodiment, the dairy product comprises evaporated milk. Evaporated milk generally comprises fresh, homogenized milk from which about 60% of the water has been removed, that has been chilled, fortified with additives such as vitamins and stabilizers, packaged, and finally sterilized. According to another particular embodiment of this invention, the dairy product comprises a dry creamer, a caloric sweetener and rebaudioside X.

In another particular embodiment, the dairy product provided herein comprises butter. Butter generally is made by churning fresh or fermented cream or milk. Butter generally comprises butterfat surrounding small droplets comprising mostly water and milk proteins. The churning process damages the membranes surrounding the microscopic globules of butterfat, allowing the milk fats to conjoin and to separate from the other parts of the cream. In yet another particular embodiment, the dairy product comprises buttermilk, which is the sour-tasting liquid remaining after producing butter from full-cream milk by the churning process.

In still another particular embodiment, the dairy product comprises cheese, a solid foodstuff produced by curdling milk using a combination of rennet or rennet substitutes and acidification. Rennet, a natural complex of enzymes produced in mammalian stomachs to digest milk, is used in cheese-making to curdle the milk, causing it to separate into solids known as curds and liquids known as whey. Generally, rennet is obtained from the stomachs of young ruminants, such as calves; however, alternative sources of rennet include some plants, microbial organisms, and genetically modified bacteria, fungus, or yeast. In addition, milk may be coagulated by adding acid, such as citric acid. Generally, a combination of rennet and/or acidification is used to curdle the milk. After separating the milk into curds and whey, some cheeses are made by simply draining, salting, and packaging the curds. For most cheeses, however, more processing is needed. Many different methods may be used to produce the hundreds of available varieties of cheese. Processing methods include heating the cheese, cutting it into small cubes to drain, salting, stretching, cheddaring, washing, molding, aging, and ripening. Some cheeses, such as the blue cheeses, have additional bacteria or molds introduced to them before or during aging, imparting flavor and aroma to the finished product. Cottage cheese is a cheese curd product with a mild flavor that is drained but not pressed so that some whey remains. The curd is usually washed to remove acidity. Cream cheese is a soft, mild-tasting, white cheese with a high fat content that is produced by adding cream to milk and then curdling to form a rich curd. Alternatively, cream cheese can be made from skim milk with cream added to the curd. It should be understood that cheese, as used herein, comprises all solid foodstuff produced by the curdling milk.

In another particular embodiment of this invention, the dairy product comprises yogurt. Yogurt generally is produced by the bacterial fermentation of milk. The fermentation of lactose produces lactic acid, which acts on proteins in milk to give the yogurt a gel-like texture and tartness. In particularly desirable embodiments, the yogurt may be sweetened with a sweetener and/or flavored. Non-limiting examples of flavorings include, but are not limited to, fruits (e.g., peach, strawberry, banana), vanilla, and chocolate. Yogurt, as used herein, also includes yogurt varieties with different consistencies and viscosities, such as dahi, dadih or dadiah, labneh or labaneh, bulgarian, kefir, and matsoni. In another particular embodiment, the dairy product comprises a yogurt-based beverage, also known as drinkable yogurt or a yogurt smoothie. In particularly desirable embodiments, the yogurt-based beverage may comprise sweeteners, flavorings, other ingredients, or combinations thereof.

Other dairy products beyond those described herein may be used in particular embodiments of this invention. Such dairy products are well known to those of ordinary skill in the art, non-limiting examples of which include milk, milk and juice, coffee, tea, vla, piima, filmjolk, kajmak, kephir, viili, kumiss, airag, ice milk, casein, ayran, lassi, and khoa.

According to particular embodiments of this invention, the dairy compositions also may comprise other additives. Non-limiting examples of suitable additives include sweeteners and flavorants such as chocolate, strawberry, and banana. Particular embodiments of the dairy compositions provided herein also may comprise additional nutritional supplements such as vitamins (e.g., vitamin D) and minerals (e.g., calcium) to improve the nutritional composition of the milk.

Rebaudioside X is also suitable for use in processed agricultural products, livestock products or seafood; processed meat products such as sausage and the like; retort food products, pickles, preserves boiled in soy sauce, delicacies, side dishes; soups; snacks such as potato chips, cookies, or the like; as shredded filler, leaf, stem, stalk, homogenized leaf cured and animal feed.

3. Concentrate Compositions

Rebaudioside X can also be provided in a concentrate composition. Suitable concentrate compositions include, but are not limited to, syrups, powdered beverages, flavor packets and flavor enhancer drops.

Beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water. Flavor packets and flavor enhancer drops are often added to beverages (e.g. water) to provide enhanced water, that is, for example, sweeter, nutrient-enriched and/or fruit-flavored.

Accordingly, in one embodiment, a concentrate composition comprising at least one sweetener and rebaudioside X is provided. When the concentrate composition is added to a beverage, the concentrate composition enhances the sweetness of said beverage by an amount more than the detectable sweetness of a solution containing the same concentration of rebaudioside X in the concentrate composition. In another embodiment, the concentrate composition enhances the sweetness of the beverage by at least about 1.0% (w/v) sucrose equivalence.

In one embodiment, a concentrate composition comprises rebaudioside X having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof. The at least one sweetener is present in a concentration above its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). Rebaudioside X is present in a concentration at or below its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The concentrate composition enhances the sweetness of the beverage by an amount more than the detectable sweetness of a solution containing the same concentration or rebaudioside X in the concentrate composition.

In one embodiment, a concentrate composition comprises rebaudioside X having a purity greater than about 95% and at least one sweetener selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof. The at least one sweetener is present in a concentration above its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). Rebaudioside X is present in a concentration at or below its sweetness recognition threshold once the concentrate composition is added to the full-strength beverage (when the concentrate composition is a flavor packet or flavor enhancer drops) or once the concentrate composition is diluted to a full-strength beverage (when the concentrate composition is a powdered beverage or syrup). The concentrate composition enhances the sweetness of the beverage by at least about 1.0% (w/v) sucrose equivalence.

The concentrate composition can further contain a liquid matrix, i.e. water, citric acid or phosphate buffer.

The concentrate composition can further contain one or more functional ingredients, detailed below. Functional ingredients include, but are not limited to, vitamins, minerals, antioxidants, preservatives, glucosamine, polyphenols and combinations thereof. Any suitable functional ingredient described herein can be used.

The concentrate composition can further contain one or more additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, weighing agents, juice, dairy, cereal and other plant extracts, flavonoids, alcohols, polymers and combinations thereof. Any suitable additive described herein can be used.

4. Additives

The sweetened compositions, beverages and/or concentrate compositions of the present invention may optionally include additional additives, detailed herein below. In some embodiments, the sweetened compositions, beverages and/or concentrate compositions contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, emulsifiers, weighing agents, gums, colorants, flavonoids, alcohols, polymers, essential oils, anti-fungal agents and combinations thereof. In some embodiments, the additives act to improve the temporal and flavor profile of the sweetener(s) to provide a taste similar to sucrose.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid ($\alpha$-, $\beta$-, and/or $\delta$-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be $\alpha$-, $\beta$-, $\gamma$- and/or $\delta$-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-$\alpha$-lysine or poly-L-$\epsilon$-lysine), poly-L-ornithine (e.g., poly-L-$\alpha$-ornithine or poly-L-$\epsilon$-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be $\alpha$-, $\beta$-, $\gamma$-, $\delta$-, and $\epsilon$-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-$\alpha$-lysine with a MW of 1,500, MW of 6,000, MW of 25,200, MW of 63,000, MW of 83,000, or MW of 300,000.

In particular embodiments, the amino acid is present in an amount effective to provide a concentration from about 10 ppm to about 50,000 ppm when present in a sweetened composition, such as, for example, a beverage. In another embodiment, the amino acid is present in in an amount effective to provide a concentration from about 1,000 ppm to about 10,000 ppm when present in a sweetened composition, such as, for example, from about 2,500 ppm to about 5,000 ppm or from about 250 ppm to about 7,500 ppm.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

The nucleotide is present in an amount effective to provide a concentration from about 5 ppm to about 1,000 ppm when present in sweetened composition, such as, for example, a beverage.

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid, 3-hydroxybenzoic acid, 3,4,5-trihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in an amount from about 10 ppm to about 5,000 ppm when present in a sweetened composition, such as, for example, a beverage.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

The inorganic acid additive is present in an amount effective to provide a concentration from about 25 ppm to about 25,000 ppm when present in a sweetened composition, such as, for example, a beverage.

Suitable bitter compound additives include, but are not limited to, caffeine, quinine, urea, bitter orange oil, naringin, quassia, and salts thereof.

The bitter compound is present in an amount effective to provide a concentration from about 25 ppm to about 25,000 ppm when present in a sweetened composition, such as, for example, a beverage.

Suitable flavorant and flavoring ingredient additives for include, but are not limited to, vanillin, vanilla extract, mango extract, cinnamon, citrus, coconut, ginger, viridiflorol, almond, menthol (including menthol without mint), grape skin extract, and grape seed extract.

"Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Dohler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

The flavorant is present in an amount effective to provide a concentration from about 0.1 ppm to about 5,000 ppm when present in a sweetened composition, such as, for example, a beverage.

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

The polymer is present in an amount effective to provide a concentration from about 30 ppm to about 2,000 ppm when present in a sweetened composition, such as, for example, a beverage.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

The protein hydrosylate is present in an amount effective to provide a concentration from about 200 ppm to about 50,000 ppm when present in a sweetened composition, such as, for example, a beverage.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

The flavonoid additive is present in an amount effective to provide a concentration from about 0.1 ppm to about 1,000 ppm when present in sweetened composition, such as, for example, a beverage.

Suitable colorants include, but are not limited to, caramel color, natural colors such as Annatto, cochineal, betanin, turmeric, paprika, saffron, lycopene, elderberry juice, pandan, yellow No. 6, yellow No. 5, red No. 40, Green No. 3 and blue No. 1.

Suitable alcohol additives include, but are not limited to, ethanol. In particular embodiments, the alcohol additive is present in the an amount effective to provide a concentration from about 625 ppm to about 10,000 ppm when present in a sweetened composition, such as, for example, a beverage.

Suitable astringent compound additives include, but are not limited to, tannic acid, europium chloride (EuCl$_3$), gadolinium chloride (GdCl$_3$), terbium chloride (TbCl$_3$), alum, tannic acid, and polyphenols (e.g., tea polyphenols). The astringent additive is present in an amount effective to provide a concentration from about 10 ppm to about 5,000 ppm when present in a sweetened composition, such as, for example, a beverage.

Suitable essential oils include, but are not limited to, mustard oil, bitter orange and sweet orange, menthe arvensis, peppermint, cedarwood, lemon, eucalyptus globulus, litsea cubeba, clove and spearmint.

Suitable anti-fungal agents include, but are not limited to, Natamycin, amphotericin, anidulafungin, caspofungin, fluconazole, itraconazole, micafungin, posaconazole, voriconazole, and flucytosine.

Other additives include typical beverages additives, i.e. glycerol ester of wood rosin, coconut oil, brominated vegetable oil, carob bean gum, sucrose acetate isobutyrate, modified food starch, zinc gluconate and vitamin A palmitate.

5. Functional Ingredients

The sweetened composition can also contain one or more functional ingredients, which provide a real or perceived heath benefit to the composition. Functional ingredients include, but are not limited to, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Antioxidant

In certain embodiments, the functional ingredient is at least one antioxidant. Generally, according to particular embodiments of this invention, the at least one antioxidant is present in the sweetened composition, e.g. concentrate composition or beverage, in an amount sufficient to promote health and wellness.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may derived from polyphenols, including prevention of cancer, heart disease, and chronic inflammatory disease and improved mental strength and physical strength, for example. Suitable polyphenols for embodiments of this invention, include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In particular embodiments, the antioxidant is a catechin such as, for example, epigallocatechin gallate (EGCG). Suitable sources of catechins for embodiments of this invention include, but are not limited to, green tea, white tea, black tea, oolong tea, chocolate, cocoa, red wine, grape seed, red grape skin, purple grape skin, red grape juice, purple grape juice, berries, pycnogenol, and red apple peel.

In some embodiments, the antioxidant is chosen from proanthocyanidins, procyanidins or combinations thereof. Suitable sources of proanthocyanidins and procyanidins for embodiments of this invention include, but are not limited to, red grapes, purple grapes, cocoa, chocolate, grape seeds, red wine, cacao beans, cranberry, apple peel, plum, blueberry, black currants, choke berry, green tea, sorghum, cinnamon, barley, red kidney bean, pinto bean, hops, almonds, hazelnuts, pecans, pistachio, pycnogenol, and colorful berries.

In particular embodiments, the antioxidant is a anthocyanin. Suitable sources of anthocyanins for embodiments of this invention include, but are not limited to, red berries, blueberries, bilberry, cranberry, raspberry, cherry, pomegranate, strawberry, elderberry, choke berry, red grape skin, purple grape skin, grape seed, red wine, black currant, red currant, cocoa, plum, apple peel, peach, red pear, red cabbage, red onion, red orange, and blackberries.

In some embodiments, the antioxidant is chosen from quercetin, rutin or combinations thereof. Suitable sources of quercetin and rutin for embodiments of this invention include, but are not limited to, red apples, onions, kale, bog whortleberry, lingonberrys, chokeberry, cranberry, blackberry, blueberry, strawberry, raspberry, black currant, green tea, black tea, plum, apricot, parsley, leek, broccoli, chili pepper, berry wine, and ginkgo.

In some embodiments, the antioxidant is resveratrol. Suitable sources of resveratrol for embodiments of this invention include, but are not limited to, red grapes, peanuts, cranberry, blueberry, bilberry, mulberry, Japanese Itadori tea, and red wine.

In particular embodiments, the antioxidant is an isoflavone. Suitable sources of isoflavones for embodiments of this invention include, but are not limited to, soy beans, soy products, legumes, alfalfa sprouts, chickpeas, peanuts, and red clover.

In some embodiments, the antioxidant is curcumin. Suitable sources of curcumin for embodiments of this invention include, but are not limited to, turmeric and mustard.

In particular embodiments, the antioxidant is chosen from punicalagin, ellagitannin or combinations thereof. Suitable sources of punicalagin and ellagitannin for embodiments of this invention include, but are not limited to, pomegranate, raspberry, strawberry, walnut, and oak-aged red wine.

In some embodiments, the antioxidant is a citrus flavonoid, such as hesperidin or naringin. Suitable sources of citrus flavonids, such as hesperidin or naringin, for embodiments of this invention include, but are not limited to, oranges, grapefruits, and citrus juices.

In particular embodiments, the antioxidant is chlorogenic acid. Suitable sources of chlorogenic acid for embodiments of this invention include, but are not limited to, green coffee, yerba mate, red wine, grape seed, red grape skin, purple grape skin, red grape juice, purple grape juice, apple juice, cranberry, pomegranate, blueberry, strawberry, sunflower, Echinacea, pycnogenol, and apple peel.

Dietary Fiber

In certain embodiments, the functional ingredient is at least one dietary fiber source. Generally, according to particular embodiments of this invention, the at least one dietary fiber source is present in the sweetened composition, e.g. concentrate composition or beverage, in an amount sufficient to promote health and wellness.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

Polysaccharides are complex carbohydrates composed of monosaccharides joined by glycosidic linkages. Non-starch polysaccharides are bonded with β-linkages, which humans are unable to digest due to a lack of an enzyme to break the β-linkages. Conversely, digestable starch polysaccharides generally comprise α(1-4) linkages.

Lignin is a large, highly branched and cross-linked polymer based on oxygenated phenylpropane units. Cellulose is a linear polymer of glucose molecules joined by a β(1-4) linkage, which mammalian amylases are unable to hydrolyze. Methylcellulose is a methyl ester of cellulose that is often used in foodstuffs as a thickener, and emulsifier. It is commercially available (e.g., Citrucel by GlaxoSmithKline, Celevac by Shire Pharmaceuticals). Hemicelluloses are highly branched polymers consisting mainly of glucurono- and 4-O-methylglucuroxylans. β-Glucans are mixed-linkage (1-3), (1-4) β-D-glucose polymers found primarily in cereals, such as oats and barley. Pectins, such as beta pectin, are a group of polysaccharides composed primarily of D-galacturonic acid, which is methoxylated to variable degrees.

Gums and mucilages represent a broad array of different branched structures. Guar gum, derived from the ground endosperm of the guar seed, is a galactomannan. Guar gum is commercially available (e.g., Benefiber by Novartis AG). Other gums, such as gum arabic and pectins, have still different structures. Still other gums include xanthan gum, gellan gum, tara gum, psylium seed husk gum, and locust been gum.

Waxes are esters of ethylene glycol and two fatty acids, generally occurring as a hydrophobic liquid that is insoluble in water.

Inulins comprise naturally occurring oligosaccharides belonging to a class of carbohydrates known as fructans. They generally are comprised of fructose units joined by β(2-1) glycosidic linkages with a terminal glucose unit. Oligosaccharides are saccharide polymers containing typically three to six component sugars. They are generally found either O- or N-linked to compatible amino acid side chains in proteins or to lipid molecules. Fructooligosaccharides are oligosaccharides consisting of short chains of fructose molecules.

Cyclodextrins are a family of cyclic oligosaccharides composed of α-D-glucopyranoside units. They can be produced from starch by means of enzymatic conversion. α-Cyclodextrin is a six sugar ring molecule, whereas β- and γ-cyclodextrins have seven and eight sugar ring molecules, respectively. Non-cyclic dextrins are known as maltodextrins and are generally easily digested by humans. Digestion resistant maltodextrin is commercially available (e.g., Fibersol-2 by ADM).

Food sources of dietary fiber include, but are not limited to, grains, legumes, fruits, and vegetables. Grains providing dietary fiber include, but are not limited to, oats, rye, barley, wheat. Legumes providing fiber include, but are not limited to, peas and beans such as soybeans. Fruits and vegetables providing a source of fiber include, but are not limited to, apples, oranges, pears, bananas, berries, tomatoes, green beans, broccoli, cauliflower, carrots, potatoes, celery. Plant foods such as bran, nuts, and seeds (such as flax seeds) are also sources of dietary fiber. Parts of plants providing dietary fiber include, but are not limited to, the stems, roots, leaves, seeds, pulp, and skin.

Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

Sources of dietary fiber often are divided into categories of soluble and insoluble fiber based on their solubility in water. Both soluble and insoluble fibers are found in plant foods to varying degrees depending upon the characteristics of the plant. Although insoluble in water, insoluble fiber has passive hydrophilic properties that help increase bulk, soften stools, and shorten transit time of fecal solids through the intestinal tract.

Unlike insoluble fiber, soluble fiber readily dissolves in water. Soluble fiber undergoes active metabolic processing via fermentation in the colon, increasing the colonic microflora and thereby increasing the mass of fecal solids. Fermentation of fibers by colonic bacteria also yields end-products with significant health benefits. For example, fermentation of the food masses produces gases and short-chain fatty acids. Acids produced during fermentation include butyric, acetic, propionic, and valeric acids that have various beneficial properties such as stabilizing blood glucose levels by acting on pancreatic insulin release and providing liver control by glycogen breakdown. In addition, fiber fermentation may reduce atherosclerosis by lowering cholesterol synthesis by the liver and reducing blood levels of LDL and triglycerides. The acids produced during fermentation lower colonic pH, thereby protecting the colon lining from cancer polyp formation. The lower colonic pH also increases mineral absorption, improves the barrier properties of the colonic mucosal layer, and inhibits inflammatory and adhesion irritants. Fermentation of fibers also may benefit the immune system by stimulating production of T-helper cells, antibodies, leukocytes, splenocytes, cytokinins and lymphocytes.

Fatty Acid

In certain embodiments, the functional ingredient is at least one fatty acid. Generally, according to particular embodiments of this invention, the at least one fatty acid is present in the sweetened composition, e.g. concentrate composition or beverage in an amount sufficient to promote health and wellness.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

Vitamin

In certain embodiments, the functional ingredient is at least one vitamin. Generally, according to particular embodiments of this invention, the at least one vitamin is present in the sweetened composition, e.g. concentrate composition or beverage, in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the sweetened compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C. Many of vitamins also have alternative chemical names, non-limiting examples of which are provided below.

| Vitamin | Alternative names |
| --- | --- |
| Vitamin A | Retinol |
| | Retinaldehyde |
| | Retinoic acid |
| | Retinoids |
| | Retinal |
| | Retinoic ester |
| Vitamin D | Calciferol |
| (vitamins D1-D5) | Cholecalciferol |
| | Lumisterol |
| | Ergocalciferol |
| | Dihydrotachysterol |
| | 7-dehydrocholesterol |
| Vitamin E | Tocopherol |
| | Tocotrienol |
| Vitamin K | Phylloquinone |
| | Naphthoquinone |
| Vitamin B1 | Thiamin |
| Vitamin B2 | Riboflavin |
| | Vitamin G |
| Vitamin B3 | Niacin |
| | Nicotinic acid |
| | Vitamin PP |
| Vitamin B5 | Pantothenic acid |
| Vitamin B6 | Pyridoxine |
| | Pyridoxal |
| | Pyridoxamine |
| Vitamin B7 | Biotin |
| | Vitamin H |
| Vitamin B9 | Folic acid |
| | Folate |
| | Folacin |
| | Vitamin M |
| | Pteroyl-L-glutamic acid |

| Vitamin | Alternative names |
| --- | --- |
| Vitamin B12 | Cobalamin |
|  | Cyanocobalamin |
| Vitamin C | Ascorbic acid |

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins.

In some embodiments, the vitamin is a fat-soluble vitamin chosen from vitamin A, D, E, K and combinations thereof.

In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

Glucosamine

In certain embodiments, the functional ingredient is glucosamine. Generally, according to particular embodiments of this invention, glucosamine is present in the sweetened composition, e.g. concentrate composition or beverage in an amount sufficient to promote health and wellness.

Glucosamine, also called chitosamine, is an amino sugar that is believed to be an important precursor in the biochemical synthesis of glycosylated proteins and lipids. D-glucosamine occurs naturally in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof. Glucosamine may be obtained by acid hydrolysis of the shells of lobsters, crabs, shrimps, or prawns using methods well known to those of ordinary skill in the art. In a particular embodiment, glucosamine may be derived from fungal biomass containing chitin, as described in U.S. Patent Publication No. 2006/0172392.

The sweetened composition can further comprise chondroitin sulfate.

Mineral

In certain embodiments, the functional ingredient is at least one mineral. Generally, according to particular embodiments of this invention, the at least one mineral is present in the sweetened composition, e.g. concentrate composition or beverage, in an amount sufficient to promote health and wellness.

Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In particular embodiments of this invention, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In other particular embodiments of this invention, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

Preservative

In certain embodiments, the functional ingredient is at least one preservative. Generally, according to particular embodiments of this invention, the at least one preservative is present in the sweetened composition, e.g. concentrate composition or beverage, in an amount sufficient to promote health and wellness.

In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

According to a particular embodiment, the preservative is a sulfite. Sulfites include, but are not limited to, sulfur dioxide, sodium bisulfite, and potassium hydrogen sulfite.

According to another particular embodiment, the preservative is a propionate. Propionates include, but are not limited to, propionic acid, calcium propionate, and sodium propionate.

According to yet another particular embodiment, the preservative is a benzoate. Benzoates include, but are not limited to, sodium benzoate and benzoic acid.

In another particular embodiment, the preservative is a sorbate. Sorbates include, but are not limited to, potassium sorbate, sodium sorbate, calcium sorbate, and sorbic acid.

In still another particular embodiment, the preservative is a nitrate and/or a nitrite. Nitrates and nitrites include, but are not limited to, sodium nitrate and sodium nitrite.

In yet another particular embodiment, the at least one preservative is a bacteriocin, such as, for example, nisin.

In another particular embodiment, the preservative is ethanol.

In still another particular embodiment, the preservative is ozone.

Non-limiting examples of antienzymatics suitable for use as preservatives in particular embodiments of the invention include ascorbic acid, citric acid, and metal chelating agents such as ethylenediaminetetraacetic acid (EDTA).

Hydration Agent

In certain embodiments, the functional ingredient is at least one hydration agent. Generally, according to particular embodiments of this invention, the at least one hydration agent is present in the sweetened composition, e.g. concentrate composition or beveage, in an amount sufficient to promote health and wellness.

Hydration products help the body to replace fluids that are lost through excretion. For example, fluid is lost as sweat in order to regulate body temperature, as urine in order to excrete waste substances, and as water vapor in order to exchange gases in the lungs. Fluid loss can also occur due to a wide range of external causes, non-limiting examples of which include physical activity, exposure to dry air, diarrhea, vomiting, hyperthermia, shock, blood loss, and hypotension. Diseases causing fluid loss include diabetes, cholera, gastroenteritis, shigellosis, and yellow fever. Forms of malnutrition that cause fluid loss include the excessive consumption of alcohol, electrolyte imbalance, fasting, and rapid weight loss.

In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In particular embodiments, the electrolytes are obtained from their corresponding water-soluble salts. Non-limiting examples of salts for use in particular embodiments include chlorides, carbonates, sulfates, acetates, bicarbonates, citrates, phosphates, hydrogen phosphates, tartates, sorbates, citrates, benzoates, or combinations thereof. In other embodiments, the electrolytes are provided by juice, fruit extracts, vegetable extracts, tea, or teas extracts.

In particular embodiments of this invention, the hydration product is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration product is a glycerol solution to enhance exercise endurance. The ingestion of a glycerol containing solution has been shown to provide beneficial physiological effects, such as expanded blood volume, lower heart rate, and lower rectal temperature.

Probiotics/Prebiotics

In certain embodiments, the functional ingredient is chosen from at least one probiotic, prebiotic and combination thereof. Generally, according to particular embodiments of this invention, the at least one probiotic, prebiotic or combination thereof is present in the sweetened composition, e.g. concentrate composition or beverage, in an amount sufficient to promote health and wellness.

Probiotics, in accordance with the teachings of this invention, comprise microorganisms that benefit health when consumed in an effective amount. Desirably, probiotics beneficially affect the human body's naturally-occurring gastrointestinal microflora and impart health benefits apart from nutrition. Probiotics may include, without limitation, bacteria, yeasts, and fungi.

According to particular embodiments, the probiotic is a beneficial microorganisms that beneficially affects the human body's naturally-occurring gastrointestinal microflora and imparts health benefits apart from nutrition. Examples of probiotics include, but are not limited to, bacteria of the genus Lactobacilli, Bifidobacteria, Streptococci, or combinations thereof, that confer beneficial effects to humans.

In particular embodiments of the invention, the at least one probiotic is chosen from the genus Lactobacilli. Lactobacilli (i.e., bacteria of the genus *Lactobacillus*, hereinafter "L.") have been used for several hundred years as a food preservative and for promoting human health. Non-limiting examples of species of Lactobacilli found in the human intestinal tract include *L. acidophilus, L. casei, L. fermentum, L. saliva roes, L. brevis, L. leichmannii, L. plantarum, L. cellobiosus, L. reuteri, L. rhamnosus, L. GG, L. bulgaricus*, and *L. thermophilus*.

According to other particular embodiments of this invention, the probiotic is chosen from the genus *Bifidobacteria*. *Bifidobacteria* also are known to exert a beneficial influence on human health by producing short chain fatty acids (e.g., acetic, propionic, and butyric acids), lactic, and formic acids as a result of carbohydrate metabolism. Non-limiting species of *Bifidobacteria* found in the human gastrointestinal tract include *B. angulatum, B. animalis, B. asteroides, B. bifidum, B. bourn, B. breve, B. catenulatum, B. choerinum, B. coryneforme, B. cuniculi, B. dentium, B. gallicum, B. gallinarum, B indicum, B. longum, B. magnum, B. merycicum, B. minimum, B. pseudocatenulatum, B. pseudolongum, B. psychraerophilum, B. pullorum, B. ruminantium, B. saeculare, B. scardovii, B. simiae, B. subtile, B. thermacidophilum, B. thermophilum, B. urinalis*, and *B.* sp.

According to other particular embodiments of this invention, the probiotic is chosen from the genus *Streptococcus*. *Streptococcus thermophilus* is a gram-positive facultative anaerobe. It is classified as a lactic acid bacteria and commonly is found in milk and milk products, and is used in the production of yogurt. Other non-limiting probiotic species of this bacteria include *Streptococcus salivarus* and *Streptococcus cremoris*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the teachings of this invention, are compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect the human body's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

Prebiotics, in accordance with the embodiments of this invention, include, without limitation, mucopolysaccharides, oligosaccharides, polysaccharides, amino acids, vitamins, nutrient precursors, proteins and combinations thereof.

According to a particular embodiment of this invention, the prebiotic is chosen from dietary fibers, including, without limitation, polysaccharides and oligosaccharides. These compounds have the ability to increase the number of probiotics, which leads to the benefits conferred by the probiotics. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, trans-galacto-oligosaccharides, and xylo-oligosaccharides.

According to other particular embodiments of the invention, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

Weight Management Agent

In certain embodiments, the functional ingredient is at least one weight management agent. Generally, according to particular embodiments of this invention, the at least one weight management agent is present in the sweetened composition, e.g. concentrate composition or beverage, in an amount sufficient to promote health and wellness.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agents is dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agents is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias,* and *Camelia*. Other embodiments include extracts derived from Gymnema Sylvestre, Kola Nut, Citrus Auran tium, Yerba Mate, Griffonia Simplicifolia, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H.*

*jutatae, H. mossamedensis, H. officinalis, H. parviflorai, H. pedicellata, H. pilifera, H. ruschii,* and *H. triebneri. Hoodia* plants are stem succulents native to southern Africa. A sterol glycoside of *Hoodia*, known as P57, is believed to be responsible for the appetite-suppressant effect of the *Hoodia* species.

In another particular embodiment, the herbal extract is derived from a plant of the genus *Caralluma*, species of which include *C. indica, C. fimbriata, C. attenuate, C. tuberculate, C. edulis, C. adscendens, C. stalagmifera, C. umbellate, C. penicillata, C. russeliana, C. retrospicens, C. Arabica,* and *C. lasiantha. Carralluma* plants belong to the same Subfamily as *Hoodia,* Asclepiadaceae. *Carralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X.

In another particular embodiment, the at least one herbal extract is derived from a plant of the genus *Trichocaulon. Trichocaulon* plants are succulents that generally are native to southern Africa, similar to *Hoodia,* and include the species *T. piliferum* and *T. officinale.*

In another particular embodiment, the herbal extract is derived from a plant of the genus *Stapelia* or *Orbea,* species of which include *S. gigantean* and *O. variegate,* respectively. Both *Stapelia* and *Orbea* plants belong to the same Subfamily as *Hoodia,* Asclepiadaceae. Not wishing to be bound by any theory, it is believed that they compounds exhibiting appetite suppressant activity are saponins, such as pregnane glycosides, which include stavarosides A, B, C, D, E, F, G, H, I, J, and K.

In another particular embodiment, the herbal extract is derived from a plant of the genus *Asclepias. Asclepias* plants also belong to the Asclepiadaceae family of plants. Non-limiting examples of *Asclepias* plants include A. incarnate, *A. curassayica, A. syriaca,* and *A. tuberose.* Not wishing to be bound by any theory, it is believed that the extracts comprise steroidal compounds, such as pregnane glycosides and pregnane aglycones, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

The at least one weight management agent may be utilized individually or in combination as a functional ingredient for the sweetened compositions provided in this invention.

Osteoporosis Management Agent

In certain embodiments, the functional ingredient is at least one osteoporosis management agent. Generally, according to particular embodiments of this invention, the at least one osteoporosis management agent is present in the sweetened composition, i.e. a concentrate composition or beverage, in an amount sufficient to promote health and wellness.

Osteoporosis is a skeletal disorder of compromised bone strength, resulting in an increased risk of bone fracture. Generally, osteoporosis is characterized by reduction of the bone mineral density (BMD), disruption of bone microarchitecture, and changes to the amount and variety of non-collagenous proteins in the bone.

In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Not wishing to be bound by any theory, it is believed that the plants and plant extracts stimulates bone morphogenic proteins and/or inhibits bone resorption, thereby stimulating bone regeneration and strength. Non-limiting examples of suitable plants and plant extracts as osteoporosis management agents include species of the genus *Taraxacum* and *Amelanchier,* as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus,* and *Anethum,* as disclosed in U.S. Patent Publication No. 2005/0079232.

Phytoestrogen

In certain embodiments, the functional ingredient is at least one phytoestrogen. Generally, according to particular embodiments of this invention, the at least one phytoestrogen is present in the sweetened composition, e.g. concentrate composition or beverage, in an amount sufficient to promote health and wellness.

Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, ginseng root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa spouts, chickpeas, peanuts, and red clover.

Long-Chain Primary Aliphatic Saturated Alcohol

In certain embodiments, the functional ingredient is at least one long chain primary aliphatic saturated alcohol. Generally, according to particular embodiments of this invention, the at least one long chain primary aliphatic saturated alcohol is present in the sweetened composition, e.g. concentrate composition or beverage, in an amount sufficient to promote health and wellness.

Long-chain primary aliphatic saturated alcohols are a diverse group of organic compounds. The term alcohol refers to the fact these compounds feature a hydroxyl group (—OH) bound to a carbon atom. The term primary refers to the fact that in these compounds the carbon atom which is bound to the hydroxyl group is bound to only one other carbon atom. The term saturated refers to the fact that these compounds feature no carbon to carbon pi bonds. The term aliphatic refers to the fact that the carbon atoms in these compounds are joined together in straight or branched chains rather than in rings. The term long-chain refers to the fact that the number of carbon atoms in these compounds is at least 8 carbons).

Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols is policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

Long-chain primary aliphatic saturated alcohols are derived from natural fats and oils. They may be obtained from these sources by using extraction techniques well known to those of ordinary skill in the art. Policosanols can be isolated from a variety of plants and materials including sugar cane (*Saccharum officinarium*), yams (e.g. *Dioscorea opposite*), bran from rice (e.g. *Oryza sativa*), and beeswax. Policosanols may be obtained from these sources by using extraction techniques well known to those of ordinary skill in the art. A description of such extraction techniques can be found in U.S. Pat. Appl. No. 2005/0220868, the disclosure of which is expressly incorporated by reference.

Phytosterols

In certain embodiments, the functional ingredient is at least one phytosterol, phytostanol or combination thereof. Generally, according to particular embodiments of this invention, the at least one phytosterol, phytostanol or combination thereof is present in the sweetened composition, e.g. concentrate composition or beverage, in an amount sufficient to promote health and wellness.

As used herein, the phrases "stanol", "plant stanol" and "phytostanol" are synonymous.

Plant sterols and stanols are present naturally in small quantities in many fruits, vegetables, nuts, seeds, cereals, legumes, vegetable oils, bark of the trees and other plant sources. Although people normally consume plant sterols and stanols every day, the amounts consumed are insufficient to have significant cholesterol-lowering effects or other health benefits. Accordingly, it would be desirable to supplement food and beverages with plant sterols and stanols.

Sterols are a subgroup of steroids with a hydroxyl group at C-3. Generally, phytosterols have a double bond within the steroid nucleus, like cholesterol; however, phytosterols also may comprise a substituted sidechain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

III. Methods

In one embodiment, the present invention provides a method for enhancing the sweetness of a sweetened composition comprising at least one sweetener in a concentration above its sweetness recognition threshold by adding rebaudioside X in a concentration at or below its sweetness recognition threshold. As stated previously, rebaudioside X enhances the sweetness of the sweetened composition by an amount more than the detectable sweetness of a solution containing the same concentration of rebaudioside X and/or enhances the sweetness of the sweetened composition by at least about 1.0% (w/v) sucrose equivalence, such as, for example from about 1.0% to about 3.0%.

Any of the sweetened compositions described above can be used.

In a particular embodiment, a method for enhancing the sweetness of a beverage comprising at least one sweetener in a concentration above its sweetness recognition threshold comprises adding rebaudioside X to said beverage in an amount at or below its sweetness recognition threshold, wherein the rebaudioside X enhances the sweetness of the beverage by an amount more than the detectable sweetness of a solution containing the same concentration of rebaudioside X and/or enhances the sweetness of the beverage by at least 1.0% sucrose equivalence, such as, for example from about 1.0% to about 3.0%.

In one embodiment, the rebaudioside X has a purity greater than 95%.

In another embodiment, the sweetener is selected from the group consisting of sucrose, fructose, glucose, high fructose corn syrup, high fructose starch syrup, D-psicose, D-allose, D-turanose, D-tagatose, D-trehalose, D-leucrose, rare sugar syrup or a combination thereof.

In still another embodiment, rebaudioside X is added in an amount to provide a final concentration of about 20 ppm to about 30 ppm in the beverage.

In another embodiment, the present invention provides a method for enhancing the sweetness of a beverage comprising at least one sweetener in a concentration above its sweetness recognition threshold by adding a concentrate composition of the present invention, i.e. a concentrate composition comprising rebaudioside X having a purity greater than about 95% and at least one sweetener selected from the group consisting of sucrose, fructose, glucose, high fructose corn syrup, D-psicose, D-allose, D-turanose, D-tagatose, D-trehalose, D-leucrose, rare sugar syrup or a combination thereof.

EXAMPLES

Example 1: Evaluation of Rebaudioside X as a Sucrose Enhancer in Beverages

Solutions were made by dissolving all ingredients in treated water. For citric acid buffer, citric acid and potassium citrate were added in a sufficient amount to bring the pH to 3.2. Finished products were filled in 300 ml-glass bottles and stored in the refrigerator. Products were prepared with the ingredients provided in Tables 1-6. The Rebaudioside X used was 95% pure and obtained from Pure Circle.

TABLE 1

| Sucrose solutions in water | | | | | | | |
|---|---|---|---|---|---|---|---|
| Ingredient (g) | 0.5% sucrose | 1% sucrose | 1.5% sucrose | 7% sucrose | 8% sucrose | 9% sucrose | 10% sucrose |
| Water | 99.5 | 99 | 98.5 | 93 | 92 | 91 | 90 |
| Sucrose | 0.5 | 1 | 1.5 | 7 | 8 | 9 | 10 |
| TOTAL | 100 g | 100 g | 100 g | 100 g | 100 g | 100 g | 100 g |

TABLE 2

| Sucrose in citric acid buffer solutions | | | | | | | |
|---|---|---|---|---|---|---|---|
| Ingredient (g) | 0.5% sucrose | 1% sucrose | 1.5% sucrose | 7% sucrose | 8% sucrose | 9% sucrose | 10% sucrose |
| Water | 99.4 | 98.9 | 98.4 | 92.9 | 91.9 | 90.9 | 89.9 |
| Citric Acid | 0.075 | 0.075 | 0.075 | 0.075 | 0.075 | 0.075 | 0.075 |
| Potassium Citrate | 0.025 | 0.025 | 0.025 | 0.025 | 0.025 | 0.025 | 0.025 |
| Sucrose | 0.5 | 1 | 1.5 | 7 | 8 | 9 | 10 |
| TOTAL | 100 g | 100 g | 100 g | 100 g | 100 g | 100 g | 100 g |

TABLE 3

Rebaudioside X in water solutions

| Ingredient (g) | 20 ppm Reb X | 30 ppm Reb X |
|---|---|---|
| Water | 100 | 100 |
| Reb X | 0.002 | 0.003 |
| TOTAL | 100 g | 100 g |

TABLE 4

Rebaudioside X in citric acid buffer solutions

| Ingredient (g) | 20 ppm Reb X | 30 ppm Reb X |
|---|---|---|
| Water | 99.9 | 99.9 |
| Citric Acid | 0.075 | 0.075 |
| Potassium Citrate | 0.025 | 0.025 |
| Reb X | 0.002 | 0.003 |
| TOTAL | 100 g | 100 g |

TABLE 5

Rebaudioside X and 7% sucrose in water solutions

| Ingredient (g) | 7% sucrose + 20 ppm Reb X | 7% sucrose + 30 ppm Reb X |
|---|---|---|
| Water | 93 | 93 |
| Sucrose | 7 | 7 |
| Reb X | 0.002 | 0.003 |
| TOTAL | 100 g | 100 g |

TABLE 6

Rebaudioside X and 7% sucrose in citric acid buffer solutions

| Ingredient (g) | 7% sucrose + 20 ppm Reb X | 7% sucrose + 30 ppm Reb X |
|---|---|---|
| Water | 92.9 | 92.9 |
| Citric Acid | 0.075 | 0.075 |
| Potassium Citrate | 0.025 | 0.025 |
| Sucrose | 7 | 7 |
| Reb X | 0.002 | 0.003 |
| TOTAL | 100 g | 100 g |

Taste Evaluation

Beverages were kept in the refrigerator overnight and tasted cold the following day. Two panelists evaluated the beverages. Bottles were removed from the refrigerator and about 50 ml of the beverage was poured in 4 oz-plastic cups. Taste test were conducted in two sessions for each type of solution: water and citric acid buffer. In the first session, the sweetness level of the beverages containing 20 ppm and 30 ppm rebaudioside X were determined against the 0.5%, 1%, and 1.5% sucrose beverages. In the second session, the sweetness level of the beverages containing 7% sucrose and either 20 ppm or 30 ppm rebaudioside X were determined against the 7%, 8%, 9%, and 10% sucrose beverages. Panelists were given mineral water for rinsing before tasting and between tasting different samples. Unsalted crackers were also given to panelists to eat followed by rinsing their mouth with mineral water before tasting the next sample.

The overall sweetness of the beverage containing 20 ppm rebaudioside X in either water or citric acid buffer was similar to the 1% sucrose beverage. Similarly, the overall sweetness of the beverage containing 30 ppm rebaudioside X in either water or citric acid buffer was similar to the 1.5% sucrose beverage. The overall sweetness of the beverage containing 7% sucrose and 20 ppm rebaudioside X in water or citric acid buffer was similar to somewhere between the 9% and 10% sucrose beverage (a 9.5% sucrose average). The overall sweetness of the beverage containing 7% sucrose and 30 ppm rebaudioside X in either water or citric acid buffer was similar to the 10% sucrose beverage.

The experiment clearly demonstrated that addition of rebaudioside X in the amount at or below its sweetness recognition threshold (20 and 30 ppm) to a beverage containing 7% sucrose resulted in a sweetness enhancement of about 1.5%.

Example 3: Evaluation of Rebaudioside X as a High Fructose Corn Syrup Enhancer in Beverages Lemon-lime carbonated soft drinks (CSD) were made by dissolving all ingredients in an amount of water sufficient to make a syrup from which finished beverages were made by adding 5.5 parts carbonated water to 1 part syrup (beverage carbonation target of 3.7 volumes of $CO_2$). Products were prepared with the ingredients provided in Table 8:

TABLE 8

| Ingredients (grams) | 8% HFCS-55 + 30 ppm Reb X (Experimental) | 8% HFCS-55 Control | 9% HFCS-55 Control | 10% HFCS-55 Control |
|---|---|---|---|---|
| Water | 88.68 | 88.68 | 87.22 | 85.75 |
| Citric Acid | 0.117 | 0.117 | 0.117 | 0.117 |
| Sodium Citrate | 0.027 | 0.027 | 0.027 | 0.027 |
| Sodium Benzoate | 0.0185 | 0.0185 | 0.0185 | 0.0185 |
| Lemon Lime Flavor | 0.087 | 0.087 | 0.087 | 0.087 |
| Reb X | 0.003 | — | — | — |
| HFCS-55 | 11.07 | 11.07 | 12.53 | 14 |
| TOTAL | 100 g | 100 g | 100 g | 100 g |

Taste Evaluation:

The beverages were aged for seven days at room temperature and then cooled at 4° C. before tasting. Four panelists evaluated the beverages. Bottles were removed from the refrigerator and about 20 ml of beverage poured in 2 oz-plastic cups. Mineral water was given for palate rinsing before tasting and between tasting different samples.

The overall sweetness of the beverage containing 8% HFCS-55 (same sweetness as 8% sucrose) and 30 ppm rebaudioside X was similar to about 10% HFCS-55 (same sweetness as 10% sucrose) in lemon lime CSD. The experiment clearly demonstrated that addition of rebaudioside X in the amount at about its sweetness recognition threshold (30 ppm) to a beverage containing 8% HFCS-55 (same sweetness as 8% sucrose) resulted in a sweetness enhancement of about 2.0%.

What is claimed is:

1. A beverage comprising a beverage matrix, at least one carbohydrate sweetener and rebaudioside X, wherein
the at least one carbohydrate sweetener is selected from the group consisting of sucrose and high fructose corn syrup, and the at least one carbohydrate sweetener is present in a concentration above its sweetness recognition threshold;

rebaudioside X has a purity from about 80% to about 99% and is present in a concentration from about 20 to about 30 ppm, and rebaudioside X enhances the sweetness of the beverage by an amount more than the detectable sweetness of a solution containing the same concentration of rebaudioside X in the absence of the at least one carbohydrate sweetener and/or the rebaudioside X enhances the sweetness of the beverage by at least about 1.0 unit of sucrose equivalence on a percentage (w/v) basis.

2. The beverage of claim 1, wherein rebaudioside X enhances the sweetness of the beverage by at least about 1.5 units of sucrose equivalence on a percentage (w/v) basis.

3. The beverage of claim 1, wherein rebaudioside X enhances the sweetness of the beverage from at least 1.0 to about 3.0 units of sucrose equivalence on a percentage (w/v) basis.

4. The beverage of claim 1, further comprising one or more functional ingredient selected from the group consisting of antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

5. The beverage of claim 1, further comprising one or more additives selected from the group consisting of carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, emulsifiers, weighing agents, gums, antioxidants, colorants, flavonoids, alcohols, polymers, essential oils, anti-fungal agents and combinations thereof.

6. The beverage of claim 1, wherein the rebaudioside X has a purity greater than about 95%.

7. The beverage of claim 1, wherein the beverage is selected from a cola, lemon-lime flavored sparkling beverage, orange flavored sparkling beverage, grape flavored sparkling beverage, strawberry flavored sparkling beverage, pineapple flavored sparkling beverage, enhanced beverage with vitamins and/or minerals, ginger-ale, soft drink, root beer, malt beverage, fruit juice, fruit-flavored juice, juice drink, nectar, vegetable juice, vegetable-flavored juice, sports drink, energy drink, protein drink, enhanced water with vitamin, near water drink, coconut water, tea, coffee, cocoa drink, beverage containing milk components, beverage containing cereal extracts and smoothie.

* * * * *